United States Patent [19]

Petrow et al.

[11] Patent Number: 5,646,136
[45] Date of Patent: Jul. 8, 1997

[54] METHODS OF INHIBITING ANGIOGENESIS AND TUMOR GROWTH, AND TREATING OPHTHALMOLOGIC CONDITIONS WITH ANGIOSTATIC AND THERAPEUTIC STEROIDS

[75] Inventors: Vladimir Petrow, Chapel Hill; Alan D. Proia, Durham, both of N.C.

[73] Assignee: Duke University, Durham, N.C.

[21] Appl. No.: 177,287

[22] Filed: Jan. 4, 1994

[51] Int. Cl.⁶ .................................. A61K 31/56
[52] U.S. Cl. .................. 514/167; 514/177; 514/178; 514/179; 514/180; 514/181; 514/912; 514/913
[58] Field of Search .................. 514/912, 913, 514/167, 177, 178, 179, 180, 181

[56] References Cited

U.S. PATENT DOCUMENTS

| 4,198,403 | 4/1980 | Alvarez | 424/241 |
|---|---|---|---|
| 4,261,986 | 4/1981 | Alvarez | 424/243 |
| 4,278,669 | 7/1981 | Alvarez | 424/243 |
| 4,285,937 | 8/1981 | Kalvoda | 424/243 |
| 4,310,466 | 1/1982 | Edwards | 260/397.1 |
| 4,599,331 | 7/1986 | Schreiber et al. | 514/179 |
| 4,617,299 | 10/1986 | Knepper | 514/178 |
| 4,686,214 | 8/1987 | Boltralik | 514/179 |
| 4,771,042 | 9/1988 | Braughler et al. | 514/171 |
| 4,917,826 | 4/1990 | Johnson et al. | 552/522 |
| 5,001,116 | 3/1991 | Folkman et al. | 514/56 |
| 5,371,078 | 12/1994 | Clark et al. | 514/182 |

FOREIGN PATENT DOCUMENTS

| 0004772 | 10/1979 | European Pat. Off. . |
| 2.974M | 11/1964 | France . |
| WO93/10141 | 5/1993 | WIPO . |

OTHER PUBLICATIONS

Folkman et al., *Angiogenesis and Inflammation*; Basic Principles and Clnical Correlates, Second Edition, pp. 821–839 (1992).

Teicher et al., *Antiangiogenic Agents Potentiate Cytotoxic Cancer Therapies Against Primary and Metastatic Disease*; Cancer Research 52, pp. 6702–6704 (1992).

International Search Report, PCT/US95/00165, May 3, 1995.

*Primary Examiner*—Brian M. Burn
*Attorney, Agent, or Firm*—Bell, Seltzer, Park & Gibson

[57] ABSTRACT

Methods for treating angiogenesis, tumors, and ocular hypertension with steroids are disclosed herein. The steroids have angiostatic activity with reduced glucocorticoid activity.

13 Claims, No Drawings

METHODS OF INHIBITING ANGIOGENESIS AND TUMOR GROWTH, AND TREATING OPHTHALMOLOGIC CONDITIONS WITH ANGIOSTATIC AND THERAPEUTIC STEROIDS

FIELD OF THE INVENTION

This invention relates generally to methods of inhibiting angiogenesis and tumor growth and treating ophthalmological conditions, and more specifically relates to methods of doing so through the administration of steroidal compounds.

BACKGROUND OF THE INVENTION

The development of new capillary blood vessels, also known as angiogenesis, occurs in normal bodily processes such as healing of wounds, growth of organs such as the corpus luteum, and growth of the embryo. Angiogenesis is also a characteristic that links many diverse diseases. See Maugh II, *Science* 212: 1374–1375 (1981); Auerback, *Lymphokines* 4: 69–68 (1981). It is a major component of some ophthalmological pathologies such as corneal graft rejection, corneal neovascularization following injury or infection, diabetic retinopathy, retrolental fibroplasia and neovascular glaucoma, Garner, *Int. Rev. Exp. Pathol* 28: 249–307 (1986), and is also a major factor in many ulcerative diseases such as rheumatoid arthritis, ulcerative colitis, and gastric ulcer. In addition, angiogenesis is a major component in pathological but nonmalignant conditions such as hemangioma, angiofibroma of the nasopharynx, avascular necrosis of bone, and psoriasis, and is further an essential requirement for tumor growth and metastasis, See, e.g., Folkman, *J. Natl. Cancer Inst.* 82: 4–6 (1990); Weidner et al., *New Engl. J. Med.* 324: 1–8 (1991).

Although originally developed for their anti-inflammatory properties, glucocorticoids are now recognized to have a wide variety of therapeutic uses. For example, many steroids with anti-inflammatory activity inhibit angiogenesis. In particular, steroids possessing the glucocorticoid side chain have been shown to inhibit angiogenesis, both alone and in conjunction with heparin, heparin fragments, or water-soluble cyclodextrin sulphate salts. See, e.g., Folkman et al., U.S. Pat. No. 5,019,562 (1991); Braughler et al., U.S. Pat. No. 4,772,042 (1988); Folkman et al., *Ann. Surg.* 206: 374–3883 (1987).

A major drawback to the use of steroids having the glucocorticoid side chain and exhibiting anti-inflammatory activity lies in the side effects that accompany their use. The side effects include, among others, immunosuppression, iatrogenic Cushing syndrome, osteoporosis, gastric ulcer, and overt diabetes mellitus.

Oxidation of the dihydroxyacetone side chain of glucocorticoids produces androstane 17β-carboxylic acids (etianic acids), which no longer possess anti-inflammatory activity, Bain et al., *Journal Steroid Biochem.* 5: 299 (1976); see also Monder et al., *Journal Steroid Biochem* 8: 897–908 (1977); Monder et al., *Recent Prog. in Hormone Res.* 36: 345–400 (1980), and which do not bind to the glucocorticoid receptor present in rat liver cytosol. Rousseau et al., *Nature* 279: 158–160 (1979). Conversion to their monoesters or 17β-acyl derivatives leads to products with marginal anti-inflammatory activity. See Phillips et al., U.S. Pat. No. 3,856,828 (1974); Alvarez, U.S. Pat. No. 4,198,403 (1980). Such mono-esters and acyl derivatives have been reported to retain angiostatic activity. See Schreiber et al., U.S. Pat. No. 4,599,331 (1986).

In light of the foregoing, it is an object of the present invention to provide alternative methods for inhibiting angiogenesis.

It is also an object of the present invention to provide alternative methods for inhibiting angiogenesis which are not accompanied by glucocorticoid activity.

It is another object of the present invention to provide alternative methods of combatting tumors with steroids, and more particularly to provide such methods using steroids with reduced corticoidal side effects.

It is an additional object of the present invention to provide alternative methods for treating ophthalmologic conditions such as ocular hypertension and glaucoma through steroidal administration.

It is a further object to provide a method of reducing glucocorticoid activity through steroidal administration.

SUMMARY OF THE INVENTION

These and other objects are satisfied by the present invention, which as a first aspect includes a method of combatting angiogenesis in a subject in need of such treatment. The method comprises administering to the subject an effective angiogenesis-combatting amount of a compound, or a pharmaceutical salt thereof, of Formula I:

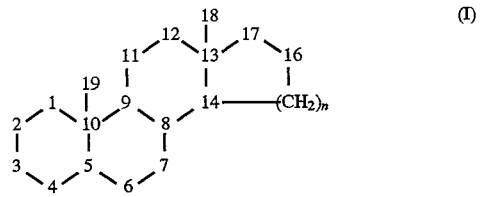

wherein the compound is optionally substituted:

at position 1 from one to two times each with halogen, hydroxyl, lower alkyl, sulfo, phosphono, carboxyl, lower alkyloxyformyl, formamido, or lower alkanoyloxy;

at positions 2 and 4 from one or two times with: halogen; lower alkyl optionally substituted with phosphono, sulfo, hydroxy, lower alkanoyloxy, succinoyl, carbamoyl, or lower alkoxy; carboxyl; lower alkyloxyformyl; formamido; hydroxy; phosphono; sulfo; lower alkoxy; lower alkanoyloxy; succinoyl; carbamoyl; or methanoyl, or one time with oxo or lower alkylidene which is unsubstituted or substituted one time with methanoyl, carboxyl, lower alkyloxyformyl, or formamido;

at position 3 one or two times with: lower alkyl optionally substituted with carboxyl, lower alkyloxyformyl, formamido, hydroxy, lower alkoxy, lower alkanoyloxy, succinoyl, carbamoyl, sulfo, phosphono, halogen, or methanoyl; hydroxyl; lower alkoxy; phosphono; sulfo; lower alkanoyloxy; succinoyl; carbamoyl; formamido; methanoyl; carboxyl; lower alkyloxyformyl; formamido; azide; or amine unsubstituted or substituted one time with lower alkyl, aryl or alkylaryl; or one time with: oxo; sulfur; oximo; lower alkyloximo; carboxymethyloximino; or lower alkylidene unsubstituted or substituted one time with alkoxy, hydroxy, lower alkanoyloxy, succinoyl, carbamoyl, sulfo, phosphono, carboxyl, lower alkyloxyformyl, or formamido;

at position 5 one time with methyl, lower alkoxy, or hydroxy;

at position 6 one or two times with: halogen; hydroxyl; lower alkoxy; lower alkanoyloxy; succinoyl; carbamoyl; sulfo; phosphono; cyano; methanoyl; oximino; lower alkyloximino; lower alkyl optionally substituted 1 to 3 times with halogen, hydroxyl, azide, or cyano; carboxyl; lower alkyloxyformyl; or formamido;

or one time with oxo, oximino, lower alkyloximino, or carboxymethyloximino;

at position 7 with lower alkyl, halogen, aryl, carboxyl, formamido, or lower alkyloxyformyl;

at position 9 one time with halogen, hydroxyl, halogenated lower alkyl, or lower alkyl;

at position 11 from one to two times with hydroxyl, lower alkoxy, lower alkanoyloxy, succinoyl, carbamoyl, halogenated lower alkanoyloxy, or lower alkyl, or one time with lower alkylidene or oxo; and at position 16 from one to two times with: lower alkyl optionally substituted one time with carboxyl, hydroxy, lower alkoxy, sulfo, or phosphono; halogenated lower alkyl; hydroxyl; lower alkoxy; lower alkanoyloxy; succinoyl; carbamoyl; sulfo; phosphono; nitroalkyl; cyano; carboxyl; lower alkyloxyformyl; formamido; or methanoyl; or one time with lower alkylidene optionally substituted one to three times with halogen or one time with oxo.

The compound is substituted at position 17 with a first substituent selected from the group consisting of: lower alkyl which is optionally substituted with hydroxy, lower alkoxy, lower alkanoyloxy, succinoyl, carbamoyl, sulfo, phosphono, methanoyl, carboxyl, lower alkyloxyformyl, formamido, or amino optionally substituted 1 or 2 times with aryl or lower alkylcarbonyl; lower alkenyl optionally substituted one time with lower alkoxy; lower alkynyl; halogen; halogenated lower alkyl; hydroxy; alkoxy; alkanoyloxy; succinoyl; carbamoyl; sulfo; phosphono; methanoyl; carboxyl; lower alkyloxyformyl; formamido; carbonyl substituted with saturated or unsaturated lower alkyl optionally substituted with hydroxy, lower alkoxy, lower alkanoyloxy, succinoyl, carbamoyl, sulfo, or phosphono, aryl, methanoyl, carboxyl, lower alkyloxyformyl, or formamido; hydroxymethyl substituted with aryl or with saturated or unsaturated lower alkyl optionally substituted with hydroxy, alkoxy, lower alkanoyloxy, succinoyl, carbamoyl, sulfo, phosphono, carboxyl, or methanoyl; aryl; aryloxy; aroyloxy; or amino optionally substituted 1 or 2 times with aryl or lower alkylcarbonyl;

The compound can be unsubstituted or substituted with a second substituent at position 17 selected from the group consisting of: hydroxy; phosphono; sulfo; lower alkanoyloxy; succinoyl; carbamoyl; saturated or unsaturated lower alkyl optionally substituted with hydroxy, lower alkoxy, lower alkanoyloxy, succinoyl, carbamoyl, phosphono, or sulfo; halogen; carboxyl; amino optionally substituted 1 or 2 times with aryl or lower alkylcarbonyl; azide; and cyano. Alternatively, the compound can be substituted one time at position 17 with oxo, oximino, lower alkyloximino, carboxymethyloximino, or lower alkylidene optionally substituted with hydroxy, lower alkanoyloxy, succinoyl, carbamoyl, methanoyl, sulfo, phosphono, carboxyl, lower alkyloxyformyl, or formamido. The compound can also be substituted so that positions 16 and 17 together form an unsubstituted or substituted isoxazolidine or methylene dioxy moiety. The compound is optionally substituted at position 18 with lower alkyl and at position 19 with lower alkyl optionally substituted with hydroxy, lower alkoxy, lower alkanoyloxy, succinoyl, carbamoyl, phosphono, sulfo, thio, lower alkylthio, lower alkylsulfo, carboxyl, lower alkyloxyformyl, formamido, or methanoyl. In the compounds of Formula I, n is 1 or 2.

The compound can be unsaturated between positions 1 and 2, 2 and 3, 3 and 4, 4 and 5, 5 and 6, 6 and 7, 8 and 9, 9 and 11, 11 and 12, 15 and 16, and 16 and 17. Also, the compound can include epoxide moieties linked to each of positions 1 and 2, 2 and 3, 3 and 4, 4 and 5, 5 and 6, 6 and 7, 8 and 9, 9 and 11, 11 and 12, 15 and 16, and 16 and 17; and further can include exocyclic methylene groups optionally substituted 1 to 2 times with halogen may be linked to each of positions 1 and 2, 2 and 3, 3 and 4, 4 and 5, 5 and 6, 6 and 7, 7 and 8, 15 and 16, and 16 and 17.

When glucocorticoid activity is undesirable, the steroids of Formula I are preferably substituted at position 17 with carboxyl, lower alkyloxyformyl, or substitute carbonyl, as these compounds have been shown to lack glucocorticoid activity. In addition, the compounds are substituted at position 6α or position 9α with halogen. Compounds so substituted have been discovered to have increased angiostatic activity. It has also been discovered that compounds substituted at position 16 with lower alkyl have increased angiostatic activity. Moreover, compounds which are unsaturated between positions 9 and 11 and compounds substituted at position 2 with carboxyl have proven to inhibit angiogenesis. Further, compounds which are unsaturated between positions 11 and 12 curb glucocorticoid activity for steroids having angiostatic activity.

A second aspect of the present invention is the use of an active compound of Formula I for the preparation of a medicament for the treatment of angiogenesis.

A third aspect of the present invention is a method of combatting tumors in a subject in need of such treatment comprising administering a tumor-combatting amount of a compound of Formula I.

A fourth aspect of the present invention is the use of an active compound of Formula I for the preparation of a medicament for the treatment of tumors.

A fifth aspect of the present invention is a method of treating ophthalmologic conditions, such as ocular hypertension and glaucoma, to a subject in need of such treatment comprising administering of a compound of Formula I.

A sixth aspect of the present invention is the use of an active compound of Formula I for the preparation of a medicament to combat ophthalmologic conditions.

DETAILED DESCRIPTION OF THE INVENTION

As set forth above, the present invention is directed to a method of combatting angiogenesis comprising administering to a subject an effective angiogenesis-combatting amount of a compound of Formula I.

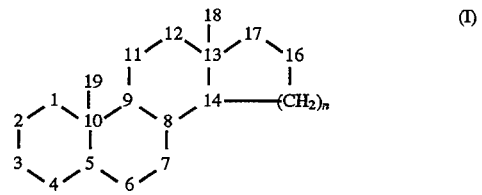

Compounds of Formula I are steroids that can be optionally substituted at indicated positions with the substituents described above. In referring to the positions of substituents of the four-ring steroid backbone, the numbering scheme recognized by those skilled in this art and indicated in Formula I is employed. Position 15, which is not explicitly indicated in Formula I, is the position in the backbone adjacent and linked to position 16. In addition, certain substituents of the steroids of the present invention are as defined hereinbelow. The term "lower alkyl" is intended to refer to an unbranched or branched alkyl group comprising between 1 and 6 carbon atoms, such as methyl, ethyl, propyl, isopropyl, n-butyl, and tert-butyl. The term "lower alkoxy" means an alkyl group of between 1 to 6 carbon atoms linked to an oxygen atom through which it is attached by an ether linkage to the steroid backbone. Exemplary lower alkoxy groups are methoxy, ethoxy, propoxy, and sec-butoxy. The term "lower alkylidene" means a branched or unbranched alkyl group comprising between 1 and 6 carbon atoms that is attached to the steroid backbone through a double bond. The term "methylene" means a methyl group that is double bonded to a position on the steroid backbone; this group may be unsubstituted or substituted with other functional groups defined herein, such as hydroxymethyl, methanoyl, and carboxyl. The term "exocyclic methylene" means a methyl group that is bonded to two different positions on the steroid backbone, such as to positions 1 and 2; exocyclic methylene groups may be unsubstituted or substituted one or two times with halogen. The term "lower alkenyl" means an unbranched or branched group comprising between 1 and 6 carbon atoms and having at least one double bond, such as ethenyl, propenyl, isopropenyl, n-butenyl, and tert-butenyl. The term "lower alkynyl" means an unbranched or branched group comprising between 1 and 6 carbon atoms and having at least one triple bond, such as ethynyl, propynyl, and n-butynyl. The term "halogen" has the meaning generally understood by those skilled in the art: namely, an atom of one of the electronegative elements of Group VIIA of the periodic table, such as fluorine, chlorine, or bromine. The term "halogenated lower alkyl" means a lower alkyl group as defined above having one or more halogen atoms. The term "alkanoyloxy" means a substituent comprising an alkyl group having a terminal carbonyl carbon that is linked to an oxygen atom; that oxygen atom is linked to the steroid backbone to form an ester therewith. The term "succinoyloxy" means a substituent that is bonded to the steroid backbone by an alkanoyloxy group having three carbon atoms which has at its other end a carboxyl group as defined below. The term "carbamoyl" means a substituent that is bonded to the steroid backbone by a 1 carbon alkanoyloxy group, wherein the carbon atom is also bonded to a nitrogen atom; the nitrogen atom can be unsubstituted or substituted 1 or 2 times with lower alkyl. A "sulfo" substituent is one comprising a sulfur atom linked to four oxygen atoms, one of which is linked to the steroid backbone. The term "phosphono" means a substituent comprising a phosphorus atom linked to four oxygen atoms, one of which is linked to the steroid backbone. The term "carboxyl" is intended to mean a carboxylic acid moiety; i.e., a carbon atom linked through a double bond to an oxygen atom, further linked to a hydroxyl group, and covalently linked to the steroid backbone. The term "lower alkyloxyformyl" is intended to mean a moiety comprising a lower alkoxy group as described above having its oxygen atom linked to a carbon atom that is double-bonded to a second oxygen atom and that is also covalently linked to the steroid backbone; thus the lower alkyl group is linked through an ester linkage to the carbon atom attached to the steroid backbone. A "methanoyl" group is an aldehyde moiety attached to the steroid backbone through the carbon atom of the aldehyde. An "oxo" substituent is intended to mean an oxygen atom double-bonded to a position on the steroid backbone, thus forming a ketone. The term "oximino" is intended to mean a nitrogen atom which is double-bonded to the steroid backbone and which is further linked to the oxygen atom of a hydroxyl group. Similarly, the term "lower alkyloximino" is intended to mean an oxime having a lower alkyl group substituted for the hydrogen atom of the hydroxyl group. The term "carboxymethyloximino" means a lower alkyloximino group having 1 carbon atom which is also bonded to a carboxyl group as defined hereinbelow. The term "lower alkoxyalkylidene" means a lower alkyl group linked through an ether linkage to a lower alkylidene group. The term "formamido" means a substituent comprising a carboxyl carbon which is linked to the steroid backbone and which is also linked to a nitrogen atom. The nitrogen atom can be substituted with one or more lower alkyl groups. The term "aryl" means aromatic homo or heterocycle substituent such as phenyl, naphthyl, phenanthryl, or pyridinyl, substituted between 1 and 5 times with lower alkyl groups. The term "carbonyl" means a moiety comprising a carbon atom linked to the steroid backbone and an oxygen atom double-bonded to the carbon atom. The carbon atom of the carboxyl group is also linked to another carbon atom of another functional group, such as substituted or unsubstituted lower alkyl. The term "hydroxymethyl" means a carbon atom linked to the steroid backbone and also linked to the oxygen atom of a hydroxyl group. The term "aryloxy" means an aromatic group, such as benzyl or naphthyl, linked to the steroid backbone through an ether linkage. The term "aroyloxy" means a substituent comprising an aromatic group linked to a carbonyl group that is linked to the steroid backbone through an oxygen atom; thus an ester links the aromatic group with the steroid backbone. For clarity, formulae representing the structures of the substituents defined by these terms and illustrating how they attach to the steroid backbone are set forth in Table 1 hereinbelow.

TABLE 1

| Functional Group Name | Structural Formula | Variables |
|---|---|---|
| lower alkyl | —R | R is linear or branched $C_1$–$C_6$ |
| lower alkoxy | —O—R | R is lower alkyl |
| lower alkylidene | =R | R is lower alkyl |
| methylene | =$CR_2$ | R is H, lower alkyl, hydroxymethyl, methanoyl, carboxyl |
| exocyclic methylene |  | R is H or halogen |
| lower alkenyl | —R—CH=CH—R | R is lower alkyl |
| lower alkynyl | —R—C≡C—R | R is lower alkyl |
| halogen | —X | X is F, Cl, or Br |
| halogenated lower alkyl | —R—X | R is lower alkyl; X is halogen |

TABLE 1-continued

| Functional Group Name | Structural Formula | Variables |
|---|---|---|
| lower alkanoyloxy | $-O-\overset{O}{\underset{\|}{C}}-R$ | H is R or lower alkyl |
| succinoyloxy | $-O-\overset{O}{\underset{\|}{C}}-CH_2-CH_2-\overset{O}{\underset{\|}{C}}-O-H$ | R is H or lower alkyl |
| carbamoyl | $-O-\overset{O}{\underset{\|}{C}}-NR_2$ | R is H or lower alkyl |
| sulfo | $-O-\overset{O}{\underset{\|}{\underset{\|}{\underset{O}{S}}}}-O-R$ | R is H or lower alkyl |
| phosphono | $-O-\overset{O}{\underset{\|}{\underset{\|}{\underset{O}{P}}}}-O-R$ | R is H or lower alkyl |
| carboxyl | $-\overset{O}{\underset{\|}{C}}-O-H$ | |
| lower alkyloxy-formyl | $-\overset{O}{\underset{\|}{C}}-O-R$ | R is lower alkyl |
| methanoyl | $-\overset{O}{\underset{\|}{C}}-H$ | |
| oxo | $=O$ | |
| oximino | $=N-O-H$ | |
| lower alkyloximino | $=N-O-R$ | R is lower alkyl |
| carboxyl-methyloximino | $=N-O-CH_2-\overset{O}{\underset{\|}{C}}-O-H$ | |
| lower alkoxy alkylidene | $-R-CH=CH-R$ | R is lower alkyl |
| formamido | $-\overset{O}{\underset{\|}{C}}-N\overset{R_1}{\underset{R_2}{\diagdown}}$ | $R_1$ and $R_2$ are hydrogen or lower alkyl |
| aryl | 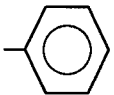 | phenyl group can be replaced with other aromatic moieties |
| carbonyl | $-\overset{O}{\underset{\|}{C}}-R$ | R is unsubstituted or substituted lower alkyl, carboxyl, hydroxymethyl, or methanoyl |
| hydroxymethyl | $-CR_2OH$ | R is H or unsubstituted or substituted lower alkyl, carboxyl, or methanoyl |
| aryloxy | 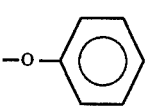 | phenyl group can be replaced with other aromatic moieties |

TABLE 1-continued

| Functional Group Name | Structural Formula | Variables |
|---|---|---|
| aroyloxy | 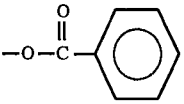 | phenyl group can be replaced with other aromatic moieties |

The term "unsaturated" within the steroid backbone indicates the presence of a double bond between the designated positions on the backbone. It will also be understood that unless otherwise designated, the substituents of the steroids of the present invention can be attached in either the "α" (i.e., extending into the page in Formula I) or the "β" (i.e., extending outwardly from the page in Formula I) stereochemical orientation relative to the steroid backbone.

The steroids used in the treatment methods of the present invention can be in the form explicitly illustrated in Formula I or can be a pharmaceutical salt thereof. The term "pharmaceutical salt" refers to a salt that retains the desired biological activity of the parent compound and does not impart undesired toxicological effects thereto. Examples of such salts are (a) salts formed with cations such as sodium, potassium, $NH_4^+$, magnesium, calcium polyamines, such as spermine, and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. Also, steroids containing oxo groups, and in particular an oxo group at position 3, can combine with carboxylate thylhydroxyl amine to form salts which are desirable for ophthalmic formulations. Steroids of Formula I having a hydroxyl group may be rendered water soluble by conversion, inter alia, to into their sulfates or phosphates salts.

The steroids to be used in the treatment methods of the present invention include those that lack the glucocorticoid side chain attached to position 17 of the steroid and in particular are those in which the glucocorticoid side chain is replaced by a carboxylic acid group and esters and amides thereof, i.e., the glucocorticoid side chain is replaced by carboxyl, lower alkyloxyformyl, or formamido as defined above. By administering steroids that lack the glucocorticoid side chain, the ability of the steroids to bind to the glucocorticoid receptor and thus cause undesirable side effects is limited or eliminated entirely. In many previous steroids examined for angiostatic activity, removal of the glucocorticoid side chain from position 17 is accompanied by a loss of angiostatic activity. The steroids employed in the treatment method of the present invention, however, are substituted so that the steroid is angiostatic but has little or no glucocorticoid activity.

At position 1, steroids of Formula I should be unsubstituted or substituted one to two times with halogen, hydroxyl, lower alkyl, sulfo, phosphono, carboxyl, lower alkyloxyformyl, formamido, or lower alkanoyloxy. It is preferred that the compound be unsubstituted at this position, particularly when an unsaturation is present between positions 1 and 2.

At position 2, steroids of Formula I can be (a) unsubstituted; (b) substituted one or two times with: halogen; lower alkyl optionally substituted with phosphono, sulfo, hydroxy, lower alkanoyloxy, succinoyl, carbamoyl, or lower alkoxy; carboxyl; lower alkyloxyformyl; formamido; hydroxy; phosphono; sulfo; lower alkoxy; lower alkanoyloxy; succinoyl; carbamoyl; or methanoyl; or (c) substituted one time with oxo or lower alkylidene which is unsubstituted or substituted one time with methanoyl, carboxyl, lower alkyloxyformyl, or formamido. It is preferred that the steroid be substituted with carboxyl, methanoyl, lower alkyl optionally substituted with hydroxy, lower alkoxy, and halogen, with carboxyl being particularly preferred. It has been determined that inclusion of an electron-attracting group, and in particular carboxyl, raises the angiostatic activity of asteroid without an accompanying rise in glucocorticoid activity. Further, compounds substituted with carboxyl at position 2 and including unsaturations between positions 1 and 2 and between positions 4 and 5 exhibit significantly reduced glucocorticoid activity and may be glucocorticoid antagonists.

Position 3 of the steroids employed with the present invention can be (a) unsubstituted; (b) substituted one or two times with: lower alkyl optionally substituted with carboxyl, lower alkyloxyformyl, formamido, hydroxy, lower alkoxy, lower alkanoyloxy, succinoyl, carbamoyl, sulfo, phosphono, halogen, or methanoyl; hydroxyl; lower alkoxy; phosphono; sulfo; lower alkanoyloxy; succinoyl; carbamoyl; methanoyl; carboxyl; lower alkyloxyformyl; formamido; azide; or amine unsubstituted or substituted one time with lower alkyl, aryl or alkylaryl, or (c) substituted one time with: oxo; sulfur; oximo; lower alkyloximo; carboxymethyloximino; or lower alkylidene unsubstituted or substituted one time with alkoxy, hydroxy, lower alkanoyloxy, sulfo, phosphono, carboxyl, lower alkyloxyformyl, or formamido. Preferably, position 3 is substituted with oxo, hydroxy, lower alkoxy, or lower alkanoyloxy, with oxo and hydroxy being particularly preferred.

At position 4, the steroids to be employed with the methods of the present invention can be (a) unsubstituted, (b) substituted one or two times with: halogen; lower alkyl optionally substituted with phosphono, sulfo, hydroxy, lower alkanoyloxy, succinoyl, carbamoyl, or lower alkoxy; carboxyl; lower alkyloxyformyl; formamido; hydroxy; phosphono; sulfo; lower alkoxy; lower alkanoyloxy; succinoyl; carbamoyl; or methanoyl, or (c) substituted one time with oxo or lower alkylidene which is unsubstituted or substituted one time with methanoyl, carboxyl, lower alkyloxyformyl, or formamido. It is preferred that position 4 be unsubstituted, particularly when unsaturations are present between positions 3 and 4 or between positions 4 and 5.

At position 5, the compounds of Formula I are unsubstituted or are substituted one time with lower alkyl, lower alkoxy, or hydroxy. Preferably, position 5 is unsubstituted.

The steroids employed by the methods of the present invention can be (a) unsubstituted at position 6; (b) substituted one or two times with: halogen; hydroxyl; lower alkoxy; lower alkanoyloxy; succinoyl; carbamoyl; sulfo; phosphono; cyano; methanoyl; oximino; lower alkyloximino; lower alkyl optionally substituted 1 to 3 times with halogen, hydroxyl, azide, or cyano; carboxyl; lower alkyloxyformyl; or formamido; or (c) substituted one time with oxo, oximino, lower alkyloximino, or carboxymethyloximino. It is preferred that, if position 6 is substituted, the substituent is in the 6α configuration. Preferred 6α substituents are those with a group such as halogen, carboxyl, lower alkyloxyformyl, formamido, cyano, or methanoyl, as it has been demonstrated that the presence of such a group at position 6α raises the angiostatic activity of the steroid without raising the glucocorticoid activity of the compound. In particular, it is preferred that position 6α be substituted with fluorine.

At position 7, the compound of Formula I can be unsubstituted or substituted with lower alkyl, halogen, aryl, carboxyl, formamido, or lower alkyloxyformyl. Preferably, position 7 is unsubstituted.

At position 9, the compound of Formula I is unsubstituted or substituted one to two times with halogen, hydroxyl, halogenated lower alkyl, or lower alkyl. It is preferred that the compound be unsubstituted or be substituted at position 9α with halogen, as it has been discovered that inclusion of a halogen atom, preferably fluorine, at this position raises the angiostatic activity of the compound.

The steroids employed by the methods of the present invention can be unsubstituted at position 11, can be substituted one to two times with hydroxyl, lower alkoxy, lower alkanoyloxy, succinoyl, carbamoyl, halogenated lower alkanoyloxy, or lower alkyl, or can be substituted one time with lower alkylidene or oxo. Preferably, the compound is substituted once with either hydroxy or oxo, or is unsubstituted if an unsaturation is present between positions 9 and 11 or between 11 and 12.

At position 16, the steroids of Formula I can be: (a) unsubstituted; (b) substituted one or two times with: lower alkyl optionally substituted one time with carboxyl, hydroxy, lower alkoxy, sulfo, or phosphono; halogenated lower alkyl; hydroxyl; lower alkoxy; lower alkanoyloxy; succinoyl; carbamoyl; sulfo; phosphono; nitroalkyl; cyano; carboxyl; lower alkyloxyformyl; formamido; or methanoyl; or (c) substituted one time with lower alkylidene optionally substituted one to three times with halogen or one time with oxo. Preferably, position 16 is occupied by lower alkyl or lower alkylidene, and it is particularly preferred that position 16 be substituted with methyl or methylene, as compounds with a methyl or methylene group at position 16 have proven to have angiostatic activity with reduced glucocorticoid activity. As noted above, position 16 can in conjunction with position 17, also form part of an isoxazolidine or methyldioxy moiety between position 16 and position 17.

The compounds of Formula I do not have the glucocorticoid side chain at position 17; consequently, binding of these compounds to the glucocorticoid receptor is substantially diminished or eliminated entirely, and thus glucocorticoid activity is substantially reduced or eliminated entirely. According to the present invention, at position 17 the steroids of Formula I are substituted with a first substituent selected from the group consisting of: lower alkyl which is optionally substituted with hydroxy, lower alkoxy, lower alkanoyloxy, succinoyl, carbamoyl, sulfo, phosphono, methanoyl, carboxyl, lower alkyloxyformyl, formamido, or amino optionally substituted 1 or 2 times with aryl or lower alkylcarbonyl; hydroxy; alkoxy; alkanoyloxy; succinoyl; carbamoyl; sulfo; phosphono; methanoyl; carboxyl; lower alkyloxyformyl; formamido; carbonyl substituted with saturated or unsaturated lower alkyl optionally substituted with hydroxy, lower alkoxy, lower alkanoyloxy, succinoyl, carbamoyl, sulfo, or phosphono, aryl, methanoyl, carboxyl, lower alkyloxyformyl, or formamido; hydroxymethyl substituted with aryl or with saturated or unsaturated lower alkyl optionally substituted with hydroxy, alkoxy, lower alkanoyloxy, succinoyl, carbamoyl, sulfo, phosphono, carboxyl, or methanoyl; or amino optionally substituted 1 or 2 times with aryl or lower alkylcarbonyl. It is preferred that the first substituent as defined above be attached at position 17β. It is also preferred that the first substituent be one having a carbonyl carbon, such as carboxyl, lower alkylformyloxy, or alkyl-substituted carbonyl, which is attached to the steroid backbones. It is particularly preferred that the first substituent be carboxyl, as compounds so substituted solubilize in water and thus can be introduced into different formulations taking many different forms, such as creams, ointments, drops, and the like.

In addition, the compound is unsubstituted or substituted at a second position with a second substituent at position 17 selected from the group consisting of: hydroxy; phosphono; sulfo; lower alkanoyloxy; succinoyl; carbamoyl; saturated or unsaturated lower alkyl optionally substituted with hydroxy, lower alkoxy, lower alkanoyloxy, succinoyl, carbamoyl, phosphono, or sulfo; halogen; carboxyl; amino optionally substituted 1 or 2 times with aryl or lower alkylcarbonyl; azide; and cyano. Preferably the second substituent is hydroxy or lower alkanoyloxy.

Position 17 can also be substituted one time with oxo, oximino, lower alkyloximino, carboxymethyloximino, or lower alkylidene which is substituted with hydroxy, lower alkanoyloxy, succinoyl, carbamoyl, sulfo, phosphono, carboxyl, methanoyl, lower alkyloxyformyl, or formamido.

Position 18 of the present invention can be substituted with lower alkyl and is preferably methyl. Position 19 can be substituted with lower alkyl optionally substituted with hydroxy, lower alkoxy, lower alkanoyloxy, succinoyl, carbamoyl, phosphono, sulfo, thio, lower alkylthio, lower alkylsulfo, carboxyl, lower alkyloxyformyl, lower alkylformamido, or methanoyl; preferably, position 19 is substituted with menthyl.

In addition, the steroids of Formula I can include unsaturations between positions 1 and 2, 2 and 3, 3 and 4, 4 and 5, 5 and 6, 6 and 7, 7 and 8, 8 and 9, 9 and 11, 11 and 12, 15 and 16, and 16 and 17. It is preferred that these unsaturations be present in particular combinations with one another and with other substituents. For example, the compound can be unsaturated between positions 4 and 5; it is preferred that along with this unsaturation, the compound also be unsaturated between positions 1 and 2, positions 6 and 7, or both. 4,6-Dienes and 1,4,6-trienes are preferably substituted at position 3 with oxo, and at position 6 with groups such as halogen, methanoyl, carboxyl or cyano, or with hydroxy, lower alkoxy, or lower alkanoyloxy (thereby forming an enol with the unsaturation between positions 6 and 7).

As another example, the compound can be unsaturated between positions 1 and 2 and between positions 3 and 4, positions 5 and 6, or both; in addition, preferred compounds have unsaturations between positions 3 and 4 and between positions 5 and 6. In compounds of this second type, it is particularly preferred that they be substituted at position 3 with hydroxy or lower alkanoyloxy and at position 6 with a moiety such as halogen, methanoyl, carboxyl, lower alkyloxyformyl, formamido, or a moiety that can form an enol with the unsaturation between positions 5 and 6, such as hydroxy, lower alkoxy, or lower alkanoyloxy.

Compounds which include unsaturations at positions 1, 4, and 8 are also preferred, particularly when the compound also includes an oxo, hydroxy, or lower alkanoyloxy group at position 3. In addition, compounds with an unsaturation between positions 11 and 12 are also preferred, particularly when unsaturations are also present between portions 1 and 2 and between portions 4 and 5. The presence of an unsaturation between positions 11 and 12 can reduce the glucocorticoid activity of a compound that has significant glucocorticoid activity.

It has also been discovered that the presence of a double bond between positions 9 and 11 in a steroid of Formula I is desirable, as the glucocorticoid activity of such compounds compared to their saturated analogs is reduced to a greater degree than the angiostatic activity of the compounds.

The steroids of Formula I can also include epoxide groups linked to the steroid backbone. These epoxide groups can be linked between any of positions 1 and 2, 2 and 3, 3 and 4, 4 and 5, 5 and 6, 6 and 7, 8 and 9, 9 and 11, 11 and 12, 15 and 16, and 16 and 17. Those skilled in this art will understand that an epoxide group should not be present at any of these positions if an unsaturation is also present. In addition, the steroids of Formula I can include exocyclic methylene groups optionally substituted 1 to 2 times with halogen that are linked between any of positions 1 and 2, 2 and 3, 3 and 4, 4 and 5, 5 and 6, 6 and 7, 7 and 8, 15 and 16, and 16 and 17.

Most preferred steroids to be employed include the following compounds:
(1) prednisolone 21-acetate
(2) prednienic acid
(3) β-methasone diproprionate
(4) 9α-fluoro-16β-methylprednienic acid
(5) 17α-Hydroxy-4-androstene-3,11 dione-17β-carboxylic acid
(6) 6α,9α-difluoro-11β-hydroxy-1,4-androstadien-3-one-17β carboxylic acid
(7) 9α-fluoro-11β-hydroxy-16α,17α-isopropylidinedioxy-3-oxo-1,4-androstadiene-17β-carboxylic acid
(8) 6α-trifluoromethyl-11-dehydrocortienic acid
(9) 3-oxo-4-etienic acid
(10) 17α-hydroxy-3-oxo-4-etienic acid
(11) 11β,17α-dihydroxy-3-oxo-4-etienic acid
(12) 11β,17α-dihydroxy-3-oxo-eti-1,4-dienic acid
(13) 11β,17α-dihydroxy-9α-fluoro-16β-methyl-3-oxo-1,4-androstadiene-17β-carboxylic acid
(14) 11β,17α-dihydroxy-6α-methyl-3-oxo-1,4-androstadiene-17β-carboxylic acid
(15) D-homo-hydrocortisone
(16) D-homocortienic acid
(17) 17-isohydrocortisone
(18) 11β,17β-dihydroxy-3-oxo-1,4-androstadiene-17α-carboxylic acid
(19) 17α-ethynyl-17β-hydroxy-1,4,9(11)-androstatrien-3-one
(20) 17β-hydroxy-21-iodo-1,4,9(11)-isopregnatriene-3,20-dione 17-acetate
(21) 17β-hydroxy-21-iodo-1,4,9(11)-isopregnatriene-3,20-dione-17-acetate
(22) 2-carboxyl-11β,17β-dihydroxy-17α-propynyl-1,4-androstadien-3-one
(23) 21-acetoxy-3-chloro-17α-hydroxy-3,5-pregnadiene-11,20-dione
(24) 3-chloro-17α-hydroxy-11-oxo-3,5-androstadiene-17β-carboxylic acid
(25) 4-chlorohydrocortisone
(26) 4-chlorocortienic acid
(27) 11β-hydroxy-16α,17α-isoxazolidyl-21-acetoxy-1,4-pregnadiene-3,20-dione
(28) 11β-hydroxy-16α,17α-isoxazolidyl-3-oxo-1,4-androstadiene-17β-carboxylic acid
(29) 6-methyl-3,11-dioxo-1,4,6-androstatriene-17β carboxylic acid 3-oxime
(30) methyl 20-dihydroprednisolonate
(31) 6-azido-9α-fluoro-16α(β)-methyl-11β,17α,21-trihydroxy-4,6 pregnadiene-3,20-dione
(32) 6-azido-11β,17α-dihydroxy-9α-fluoro-16α(β)-methyl-3-oxo-4,6-androstadiene-17β-carboxylic acid
(33) 3-methylene-11β,17α,21-trihydroxy-4-pregnene-20-one
(34) 11β,17α-dihydroxy-3-methylene-4,6-androstadiene-17β-carboxylic acid
(35) 7α-bromo-16α(β)-methyl-11β,17α,21-trihydroxy-1,4-pregnadiene-3,20-dione
(36) 7α-bromo-9α-fluoro-11β,17α-dihydroxy-16α(β)-methyl-3-oxo-1,4-androstadiene-17β-carboxylic acid
(37) 17α-acetoxy-6-cyano-16-methylene-4,6-pregnadiene-3,20-dione
(38) 6-cyano-17α-hydroxy-16-methylene-3-oxo-4,6-androstadiene-17β-carboxylic acid
(39) 4-methylcortisone
(40) 4-methyl-11-dehydrocortienic acid
(41) 17α-acetoxy-3-methoxy-6-methylpregna-3,5,7-trien-20-one
(42) 17α-hydroxy(acetoxy)-3-methoxy-6-methyl-3,5,7-androstatriene-17β-carboxylic acid
(43) 17α-acetoxy-6-hydroxymethyl-16-methylene pregna-4,6-diene-3,20-dione
(44) 6-acetoxymethyl-17α-hydroxy-16-methylene-3-oxo-4,6-androstadiene-17β-carboxylic acid
(45) 21-acetoxy-6-fluoromethyl-17α-hydroxypregna-4,6-diene-3,11,20-trione
(46) 3,11-dioxo-6-fluoromethyl-17α-hydroxy-4,6-androstadiene-17β-carboxylic acid
(47) 17α-acetoxy-16-methylene-6-piperidinomethylpregna-4,6-diene-3,20-dione
(48) 8β-cyanoprogesterone
(49) 1α-cyano-17α,21-dihydroxy-pregna-4,6-diene-3,20-dione
(50) 1α-cyano-17α-hydroxy-3-oxo-4,6-androstadiene-17β-carboxylic acid
(51) 9α-chloro-11β-azido-16α(β)-methyl-1,4-pregnadiene-17α,21-diol-3,20 dione
(52) 11β-azido-9α-chloro-17α-hydroxy-16α(β)-methyl-3-oxo-1,4-androstadiene-17β-carboxylic acid
(53) 17α-acetoxy progesterone
(54) methyl 11β-acetoxy-6α,6β-difluoro-16α-methyl-3-oxo-17α-propionyloxyandrost-4-ene 17β-carboxylate
(55) 17α-acetoxy-1α,2α-exomethylene-D-homo-4,6-pregnadiene-3,20-dione
(56) 17α-hydroxy-1α,2α-exomethylene-3-oxo-D-homo-4,6-androstadiene-17β-carboxylic acid
(57) 5α-2-pregnene-11β,17α,21-triol-20-one
(58) 11β,17α-dihydroxy-5α-2-androstene-17β-carboxylic acid
(59) 5α-3-pregnene-11β,17α,21-triol-20-one
(60) 11β,17α-dihydroxy-5α-3-androstene-17β-carboxylic acid

(61) 5β-3-pregnene-11β,17α,21-triol-20-one
(62) 11β,17α-dihydroxy-5β-3-androstene-17β-carboxylic acid
(63) 17α,20;20,21-bismethylenedioxy-11β-hydroxy pregn-4-en-3-one
(64) 17α,20,20,21-bismethylenedioxy-11β-hydroxy-2-N-piperidinome-thylenepregn-4-en-3-one
(65) 2-methylenehydrocortisone-BMD
(66) 2-methylenehydrocortisone
(67) 2-methylenecortienic acid
(68) 17α-21-dihydroxy-1,5-pregnadiene-3,20-dione 21-acetate
(69) 17α-hydroxy-3-oxo-1,5-androstadiene-17β-carboxylic acid
(70) 3-ethoxy-17α,21-dihydroxy-1,3,5-pregnatriene-11,20-dione 21-acetate
(71) 3-ethoxy-17α-hydroxy-11-oxo-1,3,5-androstatriene-17β-carboxylic acid
(72) 9α-fluoro-16α(β)-methyl-1,3,5-pregnatriene-3,17α,21-triol-11,20 dione 3,17α,21 triacetate
(73) 9α-fluoro-3-acetoxy-17α-hydroxy-16α(β)-methyl-11-oxo-1,3,5-androstatriene-17β-carboxylic acid
(74) 6-dehydroprednisolone acetate
(75) 6-dehydroprednienic acid
(76) 3β-acetoxy-16α,17α-difluoromethylene-5β-pregna-20-one
(77) 16α,17α-difluoroexomethylene-3β-hydroxy-5β-androstane-17β-carboxylic acid
(78) 3-chloro-9α-fluoro-11β,16α,17,21 tetrahydroxy-1,3,5-pregnatriene-20-on-16,17-acetonide
(79) 3-chloro-9α-fluoro-11β,16α,17α-trihydroxy-1,3,5-androstatriene-16,17-acetonide 17β-carboxylic acid
(80) 3-chloro-6,9-difluoro-11β,16α,17,21-tetrahydroxy-1,3,5-pregnatrien-20-one 16,17-acetonide
(81) 3-chloro-6,9α-difluoro-11β,16α,17α-trihydroxy-1,3,5-androstatriene-16,17-acetonide 17β-carboxylic acid
(82) 9α-fluoro-16-methyleneprednisolone
(83) 9α-fluoro-16-methyleneprednienic acid
(84) methyl 9α-fluoro-11β,17β-dihydroxy-17α-dihydroxy-16β-methyl-3-oxo-1,4-pregnadiene 17β-carboxylate
(85) 9α-fluoro-11β,hydroxy-17α-acetoxy-16β-methyl-3-oxo-1,4-androstadiene-17β-carboxylic acid
(86) 9α-fluoro-6,11β,17α,21-tetrahydroxy-16β-methyl-4,6-pregnatriene-3,20-dione 6,17,21-tripropionate
(87) 9α-fluoro-6-propionoxy-11β,17α-dihydroxy-16α(β)-methyl-3-oxo-4,6-androstadiene-17β-carboxylic acid
(88) 1,5-pregnadiene-3,11β,17α,21-tetrahydroxy-20-one
(89) 3,11β,17α-trihydroxy-1,5-androstadiene-17β-carboxylic acid
(90) 3β,11β,17α,21-tetrahydroxy-5-pregnene-20-one
(91) 3β,11β,17α-trihydroxy-5-androstene-17β-carboxylic acid
(92) 21-acetoxy-6-formyl-11β,17α-dihydroxy-3-methoxy-3,5-pregnadien-20-one
(93) 11β,17α-dihydroxy-6-formyl-3-methoxy-3,5-androstadiene-17β-carboxylic acid
(94) 16α-carboxyl-11β,21-dihydroxy-1,4-pregnadiene-3,20-dione
(95) 16α-carboxyprednienic acid
(96) 17α-acetoxy-6-methyl-16-methylene-1,4,6-pregnatriene-3,20-dione
(97) 17α-hydroxy-6-methyl-16-methylene-3-oxo-1,4,6-androstatriene-17β-carboxylic acid
(98) 17α,21-diacetoxy-6-formyl-4,6-pregnadiene-3,11,20-trione
(99) 6-formyl-17α-hydroxy-3,11-dioxo-4,6-androstadiene-17β-carboxylic acid
(100) 11β,17α,20β,21-tetrahydroxy-1,4-pregnadien-3-one
(101) 11β,17α-dihydroxy-3,20-dioxy-1,4-pregnadiene 21-oic acid
(102) 17α-acetoxy-6α-methyl progesterone
(103) 17α-hydroxy-6α-methyl-4-androstene-17β-carboxylic acid
(104) 17α-acetoxy-6-methyl-16-methylene-4,6-pregnadiene-3,20-dione
(105) 17α-hydroxy-6-methyl-16-methylene-3-oxo-4,6-androstadiene-17β-carboxylic acid
(106) 17α-acetoxy-6-methyl-16-methylene-1,4,6-pregnatriene-3,20-dione
(107) 17α-hydroxy-6-methyl-16-methylene-3-oxo-1,4,6-androstatriene-17β-carboxylic acid
(108) 17α-acetoxy-6-methyl-1,4,5-pregnatriene-3,20-dione
(109) 17α-hydroxy-6-methyl-3-oxo-1,4,6-androstatriene-17β-carboxylic acid
(110) 17α-acetoxy-6-methyl-4,6-pregnadiene-3,20-dione
(111) 17α-hydroxy-6-methyl-3-oxo-4,6-androstadiene-17β-carboxylic acid
(112) 2-carboxyl-11β,17β-dihydroxy-17α-methyl-1,4-androstadien-3-one
(113) 2-carboxyl-11β,17β-dihydroxy-17α-ethynyl-1,4-androstadiene-3-one
(114) 2-carboxyl-11β,17β-dihydroxy-17α-vinyl-1,4-androstadiene-3-one
(115) 2-carboxyl-11β,17β-dihydroxy-6α,17α-dimethyl-1,4-androstadiene-3-one
(116) 2-carboxyl-11β,17β-dihydroxy-6α-methyl-17α-ethynyl-1,4-androstadiene-3-one
(117) 2-carboxyl-11β,17β-dihydroxy-6α-methyl-17α-vinyl-1,4-androstadiene-3-one
(118) 2-carboxyl-11β,17β-dihydroxy-6α-fluoro-17α-methyl-1,4-androstadiene-3-one
(119) 2-carboxyl-11β,17β-dihydroxy-6α-fluoro-17α-ethynyl-1,4-androstadiene-3-one
(120) 2-carboxyl-11β,17β-dihydroxy-6α-fluoro-17α-vinyl-1,4-androstadiene-3-one
(121) 6-methyl-3,11β,17α,21-tetrahydroxy-5-pregnene-20-one
(122) 6-methyl-3,11β,17α-trihydroxy-5-androstene-17β-carboxylic acid
(123) 6-fluoro-3,11β,17α,21-tetrahydroxy-5-pregnene-20-one
(124) 6-fluoro-3,11β,17α-trihydroxy-5-androstene-17β-carboxylic acid
(125) 16α(β)-methyl-3,11β,17α,21-tetrahydroxy-5-pregnene-20-one
(126) 16α(β)-methyl-3,11β,17α-trihydroxy-5-androstene-17β-carboxylic acid
(127) 16α(β)-methylene-3,11β,17α,21-tetrahydroxy-5-pregnene-20-one
(128) 16α-methylene-3,11β,17α-trihydroxy-5-androstene-17β-carboxylic acid
(129) 6-fluoro-16α-methylene-3,11β,17α,21-tetrahydroxy-5-pregnene-20-one
(130) 6-fluoro-16α-methylene-3,11β,17α-trihydroxy-5-androstene-17β-carboxylic acid
(131) 6-methyl-16-methylene-3,11β,17α,21-tetrahydroxy-5-pregnene-20-one
(132) 6-fluoromethyl-16-methylene-3,11β,17α-trihydroxy-5-androstene-17β-carboxylic acid
(133) 3-(2'-fluoroethoxy)-6-formyl-9α-fluoro-17α,21-dihydroxy-11,20-dioxo-3,5-pregnadiene 21-acetate
(134) 6-formyl-9α-fluoro-17α-21-dihydroxy-3,11,20-trioxo-4,6-pregnadiene 21-acetate
(135) 6-formyl-9α-fluoro-17α-hydroxy-3,11-dioxo-4,6-androstadiene-17β-carboxylic acid (136) 6-carboxyl-9α-fluoro-17α,21-dihydroxy-3,11,20-trioxo-4,6-pregnadiene 21-acetate
(137) 9α-fluoro-17α-hydroxy-3,11-dioxo-4,6-pregnadiene-6,17β-dicarboxylic acid
(138) 2-carboxyl-prednisolone
(139) 2-carboxyprednienic acid
(140) 2-carboxyl-16α(β)-methylprednisolone
(141) 2-carboxyl-16α(β)-methylprednienic acid
(142) 2-carboxyl-16-methyleneprednisolone
(143) 2-carboxyl-16-methylene-prednienic acid
(144) 9α-fluoro-17,21-dihydroxy-1,4,11-pregnatriene-3,20-dione
(145) 17α-hydroxy-9α-fluoro-3-oxo-1,4,11-androstatriene-17β-carboxylic acid
(146) 6α,9α-difluoro-17α,21-dihydroxy-1,4,11-pregnatriene-3,20-dione
(147) 17α-hydroxy-6α,9α-difluoro-3-oxo-1,4,11-androstatriene-17β-carboxylic acid
(148) 9α-fluoro-6α-methyl-17α,21-dihydroxy-1,4,11-pregnatriene-3-20-dione
(149) 9α-fluoro-17α-hydroxy-6α-methyl-3-oxo-1,4,11-androstatriene-17β-carboxylic acid
(150) 2-formyl prednisolone
(151) 2-formylprednienic acid
(152) 2-formyl-6α-methylprednisolone
(153) 2-formyl-6α-methylprednienic acid
(154) 21-ethylprednisolone
(154) 17α,21-dihydroxy-1,4,9(11)-pregnatriene-3,20-dione
(155) 17α-hydroxy-3-oxo-1,4,9(11)-androstatriene-17β-carboxylic acid
(156) 17α,21-dihydroxy-6α-fluoro-1,4,9(11)-pregnatriene-3,20-dione
(157) 6α-fluoro-17α-hydroxy-3-oxo-1,4,9(11)-androstatriene-17β-carboxylic acid
(158) 17α,21-dihydroxy-6α-methyl-1,4,9(11)-pregnatriene-3,20-dione
(159) 17α-hydroxy-6α-methyl-3-oxo-1,4,9 (11)-androstatriene-17β-carboxylic acid
(160) 17α,21-dihydroxy-6α-fluoro-16-methylene-1,4,9(11)-pregnatriene-3,20-dione
(161) 6α-fluoro-17α-hydroxy-16-methylene-3-oxo-1,4,9(11)-androstatriene-17β-carboxylic acid
(162) 17α,21-dihydroxy-6α-fluoro-16α(β)-methyl-1,4,9(11)-pregnatriene-3,20-dione
(163) 6α-fluoro-17α-hydroxy-16α(β)-methyl-3-oxo-1,4,9(11)-androstatriene-17β-carboxylic acid
(164) prednienic acid benzylamide
(165) prednienic acid diethylamide
(166) 3,11β,17α,21-tetrahydroxy-5-pregnen-20-one
(167) 3,11β,17α-trihydroxy-5-androstene-17β-carboxylic acid
(168) 6-formyl-6-dehydro-hydrocortisone
(169) 6-formyl-6-dehydro-prednisolone
(170) 6-carboxyl-3-methoxy-11β,17α,21-trihydroxy-3,5-pregnadien-20-one
(171) 6-carboxyl-3-methoxy-11β,17α-dihydroxy-3,5-androstadiene-17β-carboxylic acid
(172) 6-carboxyl-11β,17α,21-trihydroxy-4,6-pregnadiene-3,20-dione
(173) 6-carboxyl-6-dehydrocortienic acid
(174) 6-carboxyl-11β,17α,21-trihydroxy-1,4,6-pregnatriene-3,20-dione
(175) 6-carboxyl-6-dehydroprednienic acid Those skilled in this art will appreciate that 4-enes and 1,4,6-trienes (also known as 6-dehydro-1,4-dienes) can be substituted for the above-listed 4,6-dienes.

According to the present invention, the steroids of Formula I are administered to a subject in need of angiogenesis inhibition. Conditions characterized by angiogenesis include: ophthalmological conditions such as corneal graft rejection, neovascularization following injury or infection, diabetic retinopathy, retrolental fibroplasia and neovascular glaucoma; ulcerative diseases such as rheumatoid arthritis, ulcerative colitis, and gastric ulcer; pathological, but non-malignant, conditions such as hemangioma, angiofibroma of the nasopharynx and avascular necrosis of bone; and inhibition of tumor growth and development of metastasis, see, e.g., Weidner et al., *New Engl. J. Med* 324: 1–8 (1991); Dressendörfer et al., *J. Steroid Biochem. Molec. Biol.* 43: 683–692 (1992). In addition, the method of the present invention can inhibit the angiogenesis that accompanies endometrial development, and thus can be used as a contraceptive method. Administration of these steroids can be particularly efficacious when they are administered in conjunction with drugs affecting fertility, such as estrogens, aromarase inhibitors, see Steiner, *Proc. Amer. Assoc. Cancer Res.* 33: 98 (1992), mefipristone, antiprogesterone, and the like.

The steroids of Formula I can also be administered jointly with other components such as heparin and heparin fragments, see Folkman et al., *Science* 221: 719 (1983), maltose tetrapalmitate and other glycolipids, see Benrezzak et al., *Anticancer Research* 9: 1815 (1989), and water-soluble cyclodextrin salts. See Folkman et al. U.S. Pat. No. 5,019,562.

The steroids can also be administered to inhibit angiogenesis in conjunction with anti-tumor chemotherapeutic agents such as suramin, hydralazine, and cis-diaminedichloroplatinum (II). As the blood vessels formed by tumor cells differ from normal blood cells and share some biochemical characteristics of the tumor cells themselves, therapeutic results can improve when the steroids of Formula I are administered with an agent effective against tumor cells such as: 6-methyleneprogesterone and/or 1-dehydromelengesterol acetate, for treatment of early and late prostate cancer; 6-methylene-1,4-androstadiene-3,17-dione, with or without an added antiestrogen such as tamoxifen, for treatment of mammary cancer; 6-methylene-1,4-androstadiene or 1-dehydromelengesterol acetate, for treatment of pancreatic cancer; and melengesterol acetate, for treatment of endometrial cancer.

The steroids of Formula I can also possess anti-tumor/anti-proliferative properties separate from their angiostatic properties. In vitro studies show that prednienic acid inhibits growth of the Dunning R3327 (PAP) prostatic adenocarcinoma, and that its benzylamide derivative inhibits MCF-7 breast cancer. Mickey et al, *Anti Cancer Drug Design* 5: 221–235 (1992). Prednienic acid also promotes neodifferentiation of Kirsten murine sarcoma virus transformed human skin fibroblasts into adipose cells, which assay is regarded as an indicator of anti-tumor properties. Kopelovitch et al, *Expl. Cell Biol.* 54: 25–33 (1986). The 1-dehydro-, 6-dehydro-, and 1,6-dehydro derivatives of medroxyprogesterone acetate and its 16-methylene derivatives unexpectedly have angiostatic and anti-tumor activities. 1-dehydro melegesterol acetate lacks glucocorticoid activity. 11β,17α-Dihydroxy-9α-fluoro-16β-methyl-1,4-androstadien-3-one 17β-carboxylic acid inhibits growth of the human HPAF pancreatic tumor in nude mice. Human pancreatic cancer is well known to those skilled in the art as an exceptionally malignant tumor which resists virtually all chemotherapy. 2-Carboxyl-11β,17β-dihydroxy-17α-methyl-1,4 androstadiene-3-one also inhibits certain human pancreatic cancers, and in particular inhibits those cancers rich in glucocorticoid receptors.

As noted hereinabove, the angiostatic steroids of Formula I do not exhibit significant glucocorticoid activity/toxicity; as a result, the glucocorticoid side effects stemming from systemic absorption of the steroids are significantly reduced. When it is desired to reduce further any unwanted glucocortical activity, the steroids can be administered in conjunction with an anti-glucocorticoid steroid such as 11β, 17β-dihydroxy-11α-methyl-1,4-androstadien-3-one or 2-carboxyl-11β,17β-dihydroxy-17α-methyl-1,4 androstadiene-3-one.

It may also be desirable in certain clinical conditions characterized by excess angiogenesis and inflammation to administer an angiostatic steroid which also has anti-inflammatory activity. Exemplary compounds would include steroids of Formula I substituted at positions 17α and 17β with lower alkyloxyformyl. The addition of zinc salts to steroid-containing formulations can also be advantageous in the treatment of inflammatory conditions.

The steroids of Formula I can also be used to reduce ocular hypertension in a subject in need of such treatment by administering the compounds of Formula I in an amount effective to reduce ocular hypertension. Without intending to be bound by any theory, it is believed that the steroids of Formula I can control intraocular pressure by inhibiting the accumulation or stimulating the dissolution of amorphous extracellular material in the trabecular meshwork of the eye. The presence of this amorphous extracellular material alters the integrity of the healthy trabecular meshwork and is a symptom associated with primary open angle glaucoma (POAG). It is not well understood why this amorphous extracellular material builds up in the trabecular meshwork of persons suffering from POAG. However, it has been found that the amorphous extracellular material is generally composed of glycosaminoglycans (GAGs) and basement membrane material; see, *Ophthalmology*, 90: no. 7 (1983); *May Clin. Proc.*, 61: 56–67 (1986); and *Pediat. Neurosci.*, 12: 240–251 (1985–86). When these materials build up in the trabecular meshwork, the aqueous humor, which is normally present in the anterior chamber of the eye, cannot exit the anterior chamber through the trabecular meshwork (its usual route) at its normal rate. As a result, a normal volume of aqueous humor is produced by the ciliary processes of the eye and introduced into the anterior chamber, but its exit through the trabecular meshwork is abnormally slow. Consequently, ocular hypertension results which can, if sufficiently severe, damage the optic nerve and cause blurring or even loss of vision.

The angiostatic steroids of Formula I can cause dissolution of the basement membrane scaffolding in a similar manner to that described by Ingber et al. *Endocrinology*, 119: 1768–1775 (1986). By doing so, these compounds prevent the accumulation, or promote the dissolution of, amorphous extracellular materials in the trabecular meshwork by inhibiting the formation of basement membrane materials and glycosaminoglycans. In this manner, the normal integrity of the trabecular meshwork is retained, and aqueous humor may flow through the trabecular meshwork at normal rates. As a result, the intraocular pressure of the eye can be controlled.

In the manufacture of a medicament according to the invention, hereinafter referred to as a "formulation," the compounds of Formula I are typically admixed with, among other things, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01% to 95% by weight of the active compound. One or more active compounds may be incorporated in the formulations of the invention, which may be prepared by any of the well known techniques of pharmacy consisting essentially of admixing the components.

The formulations of the invention include those suitable for oral, rectal, topical, intrathecal, buccal (e.g., sublingual), parenteral (e.g., subcutaneous, intramuscular, intradermal, or intravenous) and transdermal administration, although the most suitable route in any given case will depend on the nature and severity of the condition being treated and on the nature of the particular active compound which is being used. Formulations can also be delivered in, among others, encapsulated form, in liposomes, or in a form which includes a slow-release mechanism.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like.

Capsules, both hard and soft, are filled with compositions of these amino-amide active ingredients in combination with suitable diluents and excipients, for example, edible oils, talc, calcium carbonate and the like, and also calcium stearate.

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Liquid preparations for oral administration are prepared in water or aqueous vehicles which advantageously contain suspending agents, for example, methylcellulose, acacia, polyvinylpyrrolidone, polyvinyl alcohol and the like.

Formulations suitable for buccal (sublingual) administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations are preferably administered intravenously, although administration may also be effected by means of subcutaneous, intramuscular, intrathecal, or intradermal injection. The formulation should be sufficiently fluid that easy syringeability exists. Such preparations may conveniently be prepared by admixing the compound with water or a glycine buffer and rendering the resulting solution sterile and isotonic with the blood. Such preparations should be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal, and the like. In many cases, it is preferable to include osmotically active agents, for example, sugars or sodium chloride in isotonic concentrations. Injectable formulations according to the invention generally contain from 0.1 to 5% w/v of active compound and are administered at a rate of 0.1 ml/min/kg.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin or to the eye preferably take the form of an ointment, cream, lotion, paste, gel, spray, aerosol, or oil. Carriers which may be used include vaseline, lanoline, polyethylene glycols, alcohols, and combinations of two or more thereof. The active compound is generally present at a concentration of from 0.01 to 15% w/w, for example, from 0.01 to 2.5% w/w.

Formulations suitable for transdermal administration may be presented as discrete patches adapted to remain in intimate contact with the epidermis of the recipient for a prolonged period of time. Such patches suitably contain the active compound as an optionally buffered aqueous solution of, for example, 0.1 to 0.2M concentration with respect to the said active compound.

Formulations suitable for transdermal administration may also be delivered by iontophoresis (see, e.g., Pharmaceutical Research 3 (6), 318 (1986)) and typically take the form of an optionally buffered aqueous solution of the active compound. Suitable formulations comprise citrate or bis/tris buffer (pH 6) or ethanol/water and contain from 0.1 to 0.2M active ingredient.

In those forms in which the steroid is to be presented in solution, compounds of Formula I that contain one or more carboxyl moieties (for example, at position 17$\beta$, position 6$\alpha$, or position 2) are readily soluble in aqueous or buffer media on the alkaline side of neutrality. This solubility facilitates pharmaceutical formulation. Additionally, the esters of such compounds (i.e., those compounds having lower alkanoyloxy groups at these positions) often are valuable for depot injections.

The steroids of Formula I are administered in an amount sufficient to inhibit angiogenesis or tumor growth. The dose can vary depending on the compound selected for administration, the subject, the route of administration, and other factors. Preferably, the compound is administered in an amount of at least 0.1 ng/kg, 1 ng/kg, or 0.001 µg/kg per day or more, and is administered in an amount no greater than 1 mg/kg, 10 mg/kg, or 100 mg/kg per day, or less.

The invention is described in greater detail in the following nonlimiting examples. In these Examples, "g" means grams, "kg" means kilograms, "mg" means milligrams, "ml" means milliliters, "µl" means microliters, "°C." means degrees Celsius, "M" is molarity of solution, "N" means normality of solution, "compound S" means 17$\alpha$,21-dihydroxy-4-pregnene-3,20-dione, "mp" means melting point, "mol" means moles, "mmol" means millimoles, and "DDQ" means 2,3-dichloro-5,6-dicyanobenzoquinone.

EXAMPLE 1

Hydrolysis of Prednisone 21-acetate

Prednisone 21-acetate (5 g) is dissolved in methanol (900 ml). Potassium bicarbonate (5 g) dissolved in water (90 ml) is added at room temperature with gentle stirring. The solution is allowed to sit overnight. Most of the methanol is removed in a rotary evaporator at 35° C. using a water pump and a saturated solution of salt (50 ml). After the solution is cooled in a refrigerator at approximately 5° C. for 1 hour, the free steroid is collected, washed once with a small volume of ice water, filtered, and dried. This procedure yielded 4.3 g of the free alcohol product.

EXAMPLE 2

Hydrolysis of $\beta$-Methasone Dipropionate $\beta$-Methasone dipropionate was converted into 17$\alpha$,21-diproplonoxy-9$\alpha$-fluoro-16$\beta$-methyl-1,4,12-pregnatriene-3,20-dione by the procedure described in Avery, 3481–3486 (1964) et al., Journal Med. Chem. 33: 1852–1858 (1990). The dipropionate (4 g) in methanol (250 ml) was treated with sodium bicarbonate (25 g) under reflux for 1 hour. Saturated salt solution (700 ml) was added, and the product was extracted with two portions (500 ml and 300 ml) of chloroform. The extract was washed twice with small volumes of water, dried over magnesium sulphate, and evaporated to dryness in a Rotovapor at 35° C. The free alcohol product was produced in nearly quantitative yield.

EXAMPLE 3

Synthesis of 17$\alpha$-Hydroxy-4-androstene-3,11-dione-17$\beta$-carboxylic acid (11-dehydrocortienic acid)

Cortisone (10 g) was dissolved in methanol (500 ml) and treated with periodic acid (6.3 g) dissolved in water (125 ml). After the solution was allowed to stand overnight at room temperature, methanol was removed in a rotary evaporator, and the residue was extracted with chloroform. The chloroform solution was extracted with 5 percent bicarbonate solution and acidified with 6N hydrochloric acid to pH 2, thereby yielding of pure 11-dehydrocortienic acid.

EXAMPLE 4

Synthesis of 6$\alpha$,9$\alpha$-Difluoro-11$\beta$-hydroxy-1,4-androstadien-3-one 17$\beta$-carboxylic acid 6$\alpha$-Fluoro-dexamethasone (2 g) dissolved in methanol (100 ml) was treated with stirring overnight at room temperature with 1.5 g periodic acid in water (25 ml). The mixture was evaporated to small bulk in a rotary evaporator at 50° C. and refrigerated for 3 hours. The acid was collected by filtration and washed 3 times with small volumes of water.

The same procedure can be used to convert 6$\alpha$-fluoro-$\beta$-methasone to its 4-etienic acid.

EXAMPLE 5

Synthesis of 9$\alpha$-Fluoro-11$\beta$-hydroxy-16$\alpha$,17$\alpha$-isopropylidinedioxy-1,4-androstadiene-3-one 17$\beta$-carboxylic acid Triamcinolone acetonide (1 g) dissolved in methanol (13 ml) and ethylenedichloride (13 ml) was treated with sodium hydroxide (500 mg) in water (8 ml). Air was blown through the solution using a Pasteur pipette for 3 hours at room temperature. The aqueous layer was removed and acidified with 6N hydrochloric acid, and the precipitated acid was collected and washed with water. The resulting product was produced in a 750 mg yield. The procedure is described in greater detail in Gerasimova et al., translated from *Khimiko-Farmatsevticheskii Zurnal* 23: 1326–1329 (1988); see also, Ordzhonikidze et al., *Khimiko-Farmatsevticheskii Zurnal* 7: 39–42 (1980).

EXAMPLE 6

Synthesis of 6α-Trifluoromethyl-11-dehydrocortienic acid

Cortisone 17,21-diacetate 3-ethyl enol ether was converted into the 6β-trifluoro cortisone diacetate by the method of Lan-Hargest etal., *Tetrahedron Letts.* 278: 6557–6560 (1987). The diacetate moieties were removed following the procedure described in Example 1. The free alcohol was oxidized with periodic acid to produce the 6β-trifluoromethyl 4-etienic acid, which was converted into the 6α-isomer by standard procedures.

EXAMPLE 7

Synthesis of 3-oxo-4-etienic acid

Desoxycorticosterone (19.3 g) in ethanol (193 ml) was treated at room temperature with periodic acid (13.5 g) dissolved in water (135 ml). After a few hours at room temperature, the mixture was evaporated to small bulk under reduced pressure in a Rotovapor and left in the cold room overnight. The crystalline product was collected and crystallized from aqueous alcohol.

EXAMPLE 8

Preparation of 17α-hydroxy-3-oxo-4-etienic acid

Compound S (15.4 g) in ethanol (150 ml) was oxidized with periodic acid (11.16 g) in water (100 ml). After several hours, the mixture was collected and purified as described above in Example 7.

EXAMPLE 9

Preparation of 11β,17α-dihydroxy-3-oxo-4-etienic acid (cortienic acid)

Hydrocortisone (30 g) in ethanol (300 ml) was oxidized with periodic acid (19 g) dissolved in water (200 ml). The mixture was collected after 3 hours and purified from glacial acetic acid.

EXAMPLE 10

Preparation of 11β, 17α-dihydroxy-3-oxo-eti-1,4-dienic acid (prednienic acid)

Prednisolone (60 g) in ethanol (600 ml) was oxidized with periodic acid (40 g) dissolved in water (400 ml). After several hours the product was isolated as described above in Example 7.

EXAMPLE 11

Preparation of 11β,17α-dihydroxy-9α-fluoro-16β-methyl-3-oxo-eti-1,4-dienic acid

β-Methasone acetate (Upjohn) (5 g) in methanol (900 ml) was hydrolysed by adding potassium bicarbonate (5 g) in water (90 ml). The mixture was allowed to stand overnight at room temperature. Most of the methanol was removed in the Rotovapor under reduced pressure at 40° C. The steroid was precipitated from solution by adding saturated salt solution (50 ml). The free alcohol was collected, dried, and used directly for the oxidation stage.

β-Methasone alcohol (4.2 g) in methanol (200 ml) was oxidized with periodic acid (2.8 g) in water (28 ml). Reaction was complete in a few hours as determined by thin layer chromatography. The solution was evaporated to dryness on the Rotavapor at 50° C. under reduced pressure. The steroid in water (150 ml) was shaken with potassium hydroxide solution (2 g in 100 ml water). The resulting mixture was extracted with ether and the aqueous layer acidified to pH 4–5 with 6N hydrochloric acid. After standing to cool, the product was collected, washed with a small portion of ice-cold water, and dried.

EXAMPLE 12

Preparation of 11β,17α-dihydroxy-6α-methyl-3-oxo-eti-1,4-dienic acid

6α-Methylprednisolone (5 g) in methanol (250 ml) was oxidized with periodic acid (3.3 g) in water (30 ml). The mixture was purified from solution in aqueous potassium hydroxide followed by ether extraction and acidification.

EXAMPLE 13

Preparation of D-Homo-hydrocortisone

16α, 17α-Cyclomethylene-4,9(11)-pregnadiene-3,20-dione was prepared from 4,9(11), 16-pregnatriene-3,20-dione by reaction with trimethylsulfoxonium iodide/sodium hydride. This intermediate was converted into D-homo-4,9 (11), 17-pregnatriene-3,20-dione by reaction with perchloric acid in acetic anhydride solution. The latter was converted into D-homo-1,4,9(11)-17α-hydroxy-pregnatriene-3,20-dione by the method set forth in U.S. Pat. No. 4,036,874 to Alig et al., and the crude product was acetylated to give the 21-acetoxy-derivative. Conversion into the 9(11)-epoxy derivative via the bromohydrin method followed by hydrolysis of the epoxide moiety produced D-homo-hydrocortisone having a melting point of approximately 210° C.

EXAMPLE 14

Preparation of 17-Isohydrocortisone and its 9: 11-ene

A. Preparation of 17α-Ethynyl-17β-hydroxy-1,4,9(11)-androstatrien-3-one

In a three-necked flask, 95 percent potassium hydroxide (200 g), tetrahydrofuran (1000 ml) and ethanol (120 ml) were stirred at 50° C. for 1 hour under a nitrogen atmosphere and then cooled to 3° C. Into the mixture prepared as above, pure dry acetylene was passed at 3° C. for 2 hours. A solution of 1,4,9(11)-androstatriene-3,17-dione (100 g) in 200 ml of dry tetrahydrofuran was added and stirred for 2 hours. The mixture was acidified with 10 percent aqueous Hcl solution, stirred under reflux for half an hour, and diluted with water. The resulting precipitated product was collected by filtration, washed with water, and dried to give 17α-ethynyl-17β-hydroxyandrosta-1,4-dien-3-one (110.3 g, purity 92.9 percent, yield 96.6 percent).

B. Preparation of 17β-hydroxy-21-iodo-1,4,9(11)-isopregnatatriene-3,20-dione 17-acetate To a mixture prepared by adding iodine (0.408 g), acetic acid (4.5 ml), and water (0.5 ml) to 17α-ethynyl-17β-hydroxy-1,4,9(11)-androstatriene-3-one 17-acetate (0.571 g), a mixture of 40 percent peracetic acid (0.26 ml), acetic acid (16 ml) and water (2 ml) was added dropwise and stirred at room temperature for 2 hours. The reaction mixture was poured into water (150 ml) and the resulting precipitate was collected with filtration, washed with water and dissolved in dichloromethane. The solution was washed successively with 7 percent aqueous KI solution, 10 percent aqueous sodium thiosulfate solution and water, dried over anhydrous sodium sulfate, and concentrated to give crude 21,21-di-iodo-17β-hydroxy-1,4,9(11)-isopregnatriene-3,20-dione 17-acetate (0.961 g).

To this crude iodide (0.200 g), triethylamine (0.83 ml), acetic acid (0.53 ml), and acetone (5 ml) were added and stirred under reflux for 1 hour. The reaction mixture was poured into water (100 ml) and the resulting precipitate was collected by filtration and dried to give 17β-hydroxy-21-iodo-1,4,9(11)-isopregnatriene-3,20-dione 17-acetate (0.142 g). Without further purification, this crude iodide was used in Step C below.

C. Preparation of 17β,21-dihydroxy-21-iodo-1,4,9(11)-isopregnatriene-3,20-dione 17-acetate To 17β-hydroxy-21-iodo-1,4,9(11)-iso-pregnatriene-3, 20-dione 17-acetate (2.01 g), N-methylpyrrolidone (6.0 ml) and tetramethylammonium acetate (0.80 g) were added and stirred at 21° C. for 7 hours. Thereafter, 60ml of water was slowly dripped while agitating. The resulting crystal was filtered off, washed with water, and dried to obtain 1.64 g of crystals. Recrystallization from ethanol (16 ml) yielded 17β,21-dihydroxy-1,4,9(11)-isopregnatriene-3,20-dione 17,21-diacetate.

D. Preparation of 17-Iso-11-dehydrocortienic acid

Hydrolysis of 17β,21-dihydroxy-1,4,9(11)-isopregnatriene-3,20-dione 17β,21-diacetate with potassium bicarbonate gave the 17β,21-diol, which was then oxidized to the 17α-carboxylic acid with periodic acid.

Employing standard reactions the diacetate was converted into the 9(11)-epoxide and thence into 11β,17β,21-trihydroxy-1,4-isopregnadiene-3,20-dione, the 11-oxo derivative, and the corresponding 17β-carboxylic acids.

EXAMPLE 15

Preparation of 17α-Acetoxy-6-methyl-16-methylene-1,4 6-pregnatriene-3,20-dione 4 g Melengesterol acetate (Upjohn) and 4 g dichlorodicyanobenzoquinone were dissolved in 200 ml dioxane and the solution refluxed for 18 hours. The mixture was diluted with ether (600 ml) and, after standing overnight at room temperature, the precipitated hydroquinone was removed by filtration. The solution was washed with dilute aqueous KOH until the washings were colorless; the ether solution was then washed with water and dried. Removal of the solvent left a pale brown solid which was crystallized from aqueous ethanol (mp 228°–232°, yield approximately 70 percent).

EXAMPLE 16

Preparation of 17α,21-Diacetoxy-6-formyl-4,6-pregnadiene-3,11,20-trione

Following the procedure set forth in Great Britain Patent No. 929,983 to Kirk et al., the 3-methyl enol ether of cortisone diacetate was converted into the 6-formyl derivative. To a solution of 1 g of the 6-formyl derivative in tetrahydrofuran (20 ml) cooled to 0° C. was added 1.05 molar equivalents of 2,3-dichloro-5,6-dicyanobenzoquinone and p-toluene sulphonic acid (100 mg). The resulting mixture was stirred at 0° C. for 30 minutes, filtered, and diluted with methylene chloride (100 ml). The organic phase was separated, washed with 5 percent aqueous sodium hydroxide until the washings were colorless, washed again with water, and evaporated to dryness, leaving as a faintly colored crystalline solid 17α,21-diacetoxy-6-formyl-4,6-pregnadiene-3,11,20-trione. Purification required one crystallization from aqueous methanol.

Careful oxidation of the product with Jones reagent or with silver oxide can produce the 6-carboxylic acid derivative of this compound.

EXAMPLE 17

Preparation of 11β, 17α-dihydroxy-17β-formyl-1,4 pregnadien-3-one

A. Preparation of 11β,17α,20β,21-Tetrahydroxy-1, 4-pregnadien-3-one

Prednisolone acetate (2 g) in 400 ml methanol at 0° C. was treated with sodium borohydride (290 mg). After stirring for 1.5 hours, acetic acid (2 ml) was added and the mixture evaporated to dryness. The solid residue was extracted with chloroform, and the extract was washed twice with 1N potassium hydroxide solution, once with water, then evaporated. The product (7.84 g) was hydrolysed in methanol (800 ml) with potassium bicarbonate (7.84 g) in water (50 ml) to produce the free triol, which appeared as a single spot on thin layer chromatography.

B. Oxidation of 11β,17α,20β,21-Tetrahydroxy-1, 4-pregnadien-3-one to the 17β-Formyl Derivative The total product produced in Section A above was dissolved in dioxane (1000 ml) and oxidized with periodic acid (4.7 g) dissolved in water (200 ml), with dioxane (200 ml) also being added dropwise with stirring. The mixture was left approximately 72 hours at room temperature. The mixture was diluted with an equal volume of water and evaporated in a Rotovapor. One recrystallization of the solid residue from ethanol/acetone gave 11β,17α,-dihydroxy-17β-formyl-1,4-pregnadien-3-one which produced a single spot on thin layer chromatography.

EXAMPLE 18

Preparation of 1,4,11-triene derivatives from Dexa- and Beta-Methasone

A. Preparation of 9α-Fluoro-17α-21-dipropionoxy-16α-methyl-1,4,11-pregnatriene-3,20-dione Dexamethasone dipropionate (2 g) in dioxane (30 ml) at 15° C. was treated dropwise with 1.8 ml of diethylaminosulphur trifluoride (Carbolabs Inc) over 30 minutes; the mixture was then left at room temperature for 3 hours. Saturated sodium bicarbonate solution was cautiously added in excess and the product precipitated with water. One recrystallization from a solvent comprising 15 parts ethanol/ 10 points acetone produced pure 9α-Fluoro-17α-21-dipropionoxy-16α-methyl-1,4,11-pregnatriene-3,20-dione product (mp 166°–167° C.).

B. Preparation of 9α-fluoro-17α,21-diacetoxy-16β-methyl-1,4,11-pregnatriene-3,20-dione Under the conditions described in Section A above, using β-methasone as the starting material produced 9α-fluoro-17α,21-diacetoxy-16β-methyl-1,4,11-pregnatriene-3,20-dione (mp 135°–136° C.).

C. Preparation of 17β-carboxyl io acids of Dexa- and Beta-Methasone Derivatives

Both of the steroids produced in Sections A and B above were hydrolysed with sodium bicarbonate to give the corresponding 17α,21-diols. Each of these compounds were oxidized with periodic acid to the corresponding 17β-carboxylic acids.

EXAMPLE 19

Preparation of N-(2-hydroxyethyl)-α-(17β-hydroxy-3-methoxypregna-3,5-dien-6-yl)nitrone A mixture of hydrocortisone (30.6 g, 0.1 mol), NaHCO$_3$ (35 g), and N-methylhydroxylamine oxalate (18.9 g, 0.1 mol) in absolute ethanol (75 ml) was stirred overnight in the dark under reflux. The reaction mixture was filtered and the filtrate was concentrated. The residue was chromatographed on silica gel (350 g) and eluted with acetone to produce pale yellow crystals of the nitrone.

EXAMPLE 20

Preparation of 3-Methylene Steroids

To a suspension of methyltriphenylphosphonium bromide (4 mmol) in anhydrous ether, n-butyllithium (4 mmol) in n-hexane was added slowly with stirring at room temperature under a nitrogen atmosphere. The mixture was stirred for 20 minutes and then prednisolone BMD (1 mmol) dissolved in anhydrous ether was added, and the stirring was continued overnight. The ether was then removed by distillation and was replaced by anhydrous tetrahydrofuran. The mixture was then refluxed for 1.5 hours, diluted with chilled water, and extracted with ethyl acetate. The organic layer was washed with water, dried over anhydrous sodium sulfate, and evaporated. The residue was purified by silica gel column chromatography.

EXAMPLE 21

Preparation of 2-ene and 3-ene Steroids

A. Preparation of 5α-2-Pregnene-11β,17α,21-triol-20-one

3β-Hydroxytosyl-5α-pregna-11β,17α,21-triol-20-one was subjected to reaction with sodium acetate in acetic acid-acetic anhydride, which reaction produced 5α-2-pregnene-11β,17α,21-triol-20-one.

B. Preparation of 5α-3-Pregnene-11β,17α,21-triol-20 one and its 5β-analog

The 3-tosyl hydrazone of hydrocortisone-BMD was reduced with sodium cyanoborohydride. The BMD protective group was then removed. The mixture of 5α- and 5β isomers of 5-3-pregnene-11β,17α,21-triol-20-one was chromatographically separated into its constituent stereoisomers on a silica column.

EXAMPLE 22

Preparation of 6-Dehydro Prednisolone Acetate

Prednisolone enol acetate in dioxane solution is treated at room temperature with 1.1M equivalents of DDQ dissolved in dioxane, and the mixture is left at room temperature for approximately 72 hours. The precipitated dihydroquinone is filtered off and the mixture is diluted with water and extracted with a large volume of ether. The ethereal solution is washed with 5 percent potassium hydroxide solution until the washings are colorless, then washed with water, dried, and evaporated to dryness. The residual 1,4,6-triene (6-dehydro prednisolone acetate) is crystallized from aqueous methanol and is generally pure after one crystallization (mp 210°–211° C.).

EXAMPLE 23

Preparation of Prednienic Acid Benzylamide

A solution of prednienic acid (330 mg), dicyclohexylcarbodiimide (227 mg) and hydroxybenzotriazole (203 mg) in methylene chloride was stirred overnight in the cold room. The precipitated dicyclohexylurea was removed by filtration and benzylamine (0.1 ml) was added. After chilling overnight in the cold room, the solution was extracted with 0.1M sodium bicarbonate, then with 1N HCl, and washed twice with water. The dried organic layer was evaporated and the residue crystallized from methanol-ethyl acetate. The product, prednienic acid benzamide, had a melting point of 147°–148° C.

EXAMPLE 24

In Vivo Determination of Angiostatic Activity

The ability of etianic acids to inhibit angiogenesis was evaluated in vivo in rats. Each animal had its corneas cauterized with silver nitrate/potassium nitrate. The cauterization causes the normally avascular cornea to undergo neovascularization (angiogenesis). This animal model, refined by Proia et al., Lab. Invest. 58: 473–479 (1988) and now a well-established assay, quantifies corneal neovascularization by computerized image analysis. It has been used for demonstrating that corticosteroids (and to a lesser extent nonsteroidal anti-inflammatory drugs) inhibit neovascularization, Haynes et al., Invest. Ophthalmol. Vis. Science 30: 1588–1593 (1989), and can provide a more definitive evaluation of angiostatic activity than models using the chorioallantoic membrane in the chick egg or the rabbit eye model. See Proia et al., Exp. Eye Res. (in press—to be published in Vol. 57 in 1993).

Female rats were obtained from Zivic-Miller Laboratories, Zelienople, Pa. There were 6–8 rats included in each treatment group. Neovascularization was induced by cauterizing both corneas of each anesthetized rat; this was performed by applying the tip of a silver nitrate/potassium nitrate to the cornea for 5–7.5 seconds.

The corneal tissues were treated with steroid formulations. The steroids included in the formulations tested are listed in Table 2.

TABLE 2

| Steroids assessed for angiogenesis inhibition | |
|---|---|
| compound number | structure |
| 527 | 17β-carboxyl-17α-hydroxy-4-androsten-3,11-dione |
| 525 | 17β-carboxyl-11β-hydroxy-4-androsten-3one |
| 517 | 17β-carboxyl-11β,17α-dihydroxy-6α-methyl-1,4-androstadien-3-one |
| 518 | 17β-carboxyl-11β,17α-dihydroxy-9α-fluoro-16α-methyl-1,4-androstadien-3-one |
| 526 | 17β-carboxyl-3α,11β,17α-trihydroxy-androstane |
| 513 | 17β-carboxyl-11β,17α-dihydroxy-9α-fluoro-16β-methyl-1,4-androstadien-3-one |
| 2013 | 17β-carboxyl-11β,17α-dihydroxy-3-oxo-1,4-androstadiene |
| 532 | 6,9-difluoro-11β,17-dihydroxy-16α-methylpregna-1,4-diene-3-one-17β-carboxylic acid |
| 1000 | 4-androsten-3-one-17β-carboxylic acid |
| 323 | 17β-carboxyl-11β,17α-dihydroxy-4-androsten-3-one |

Steroids were formulated in vehicle containing 10 percent Tween 20 (polyoxyethylene sorbitan monolaurate) dissolved in 0.9 percent saline with percent (by volume) 0.2M tris (hydroxymethyl)aminomethane, pH 7.4. The steroids dissolved readily when the pH was adjusted to 7.0–8.0 with NaOH or KOH. All steroids were tested at a concentration of 1 percent; additionally, some formulations were also tested at 0.01 percent, 0.1 percent, and 2.5 percent. Three 10 μl drops of each concentration of steroid were applied topically to each cauterized cornea four times per day (8:00 a.m., noon, 4:00 p.m., and 8:00 p.m.).

After four days of treatment, the animals were euthanized by rapid asphyxiation in a carbon dioxide chamber. The vasculature was perfused with a mixture of 10 percent india ink/11 percent gelatin/lactated Ringer's solution. Corneal tissue was dissected and prepared as flat mounts. During dissection, the corneas were examined with a dissecting microscope, and the degree of neovascularization was graded numerically from 1+ to 4+. After dehydration with alcohols, cleaning with xylene, mounting, and drying, the area of each cornea and the length of blood vessels were determined by computerized image analysis.

Statistical evaluation of inhibition of corneal neovascularization by each concentration of drug was evaluated using Mann Whitney U Tests (one-tailed; P<0.05=significant difference). In general, meaningful inhibition of angiogenesis can be detected using the subjective rating scale. In all cases, however, image analysis was used to quantitatively confirm visual observations.

EXAMPLE 25

Results of Angiogenesis Inhibition Assessment

Angiostatic activity in the rat eye assay was particularly evident in the prednienic type of structure. Furthermore, it was enhanced by introduction of 16β-methyl groups. The 16α-Me group was less effective in increasing angiostatic activity, but such activity was usually enhanced by introduction of a 6α-substituent.

Of the steroids tested following the procedure described in Example 24, compounds 527, 525, 517, 518, 526, and 1000 did not significantly inhibit corneal vascularization when applied topically. Compounds 513, 2013, 323, and 532 did cause significant inhibition of corneal vascularization. More detailed data for the procedures in which these compounds effected such results are described individually below.

A. 17β-carboxylic acid derivative of betamethasone (compound #513). Only subjective angiogenesis scores were collected for this steroid. The mean ±1 standard deviation (S.D.) for the angiogenesis scores (using the averages of the two eyes of each rat), average percent inhibition of neovascularization, number of rats per group, and p value (versus vehicle) are shown in Table 3.

TABLE 3

Corneal Angiogenesis for Compound 513

| Formulation | Score | Percent Inhibition | n | p |
|---|---|---|---|---|
| Vehicle | 1.8 ± 0.6 | — | 8 | — |
| 0.01% #513 | 1.8 ± 0.4 | 0 | 7 | NS |
| 0.1% #513 | 1.1 ± 0.9 | 39% | 7 | NS |
| 1.0% #513 | 0.4 ± 0.4 | 78% | 7 | 0.0002 |

The degree of inhibition of corneal angiogenesis by 1 percent compound 513 appeared similar to that caused by topically applied 0.1 percent dexamethasone sodium phosphate. In contrast to topically applied dexamethasone, there was no significant loss of body weight in the rats treated with 1.0 percent compound 513. Thymus weights in rats treated topically with 1 percent compound 513 were 0.187±0.042 gm, which represents an average 45 percent decrease from control thymus weights of 0.337±0.077 gm (p=0.0002). Topical 0.1 percent and 0.01 percent compound 513 did not cause any significant change in thymus weight. For comparison, topical application of 0.1 percent dexamethasone reduced thymus weight by 75 percent in a similar experiment.

The ability of 1.0 percent compound 513 to reduce angiogenesis to approximately the same level as 0.1 percent dexamethasone with diminished thymus weight reduction suggests a preferred therapeutic profile for this compound than for dexamethasone. It also indicates a high probability that refinements in the steroids may provide complete separation of anglostatic and glucocorticoid activities.

B. 17β-carboxylic acid derivative of prednisolone (compound 2013). Two studies, using different synthetic lots of compound 2013, have quantitatively demonstrated this compound's ability to inhibit corneal neovascularization. The mean ±1 standard deviation for corneal neovascularization (expressed as percent of the corneal area occupied by blood vessels), average percent inhibition of neovascularization, number of rats per group, and p values (versus vehicle controls) for each experiment are shown in Table 4.

TABLE 4

Data of Assessment of Corneal Angiogenesis for Compound 2013

| Compound | Neovascularization | Percent Inhibition | n | p |
|---|---|---|---|---|
| Experiment A | | | | |
| Vehicle | 21.5 ± 6.3% | — | 5 | — |
| 0.01% #2013 | 26.2 ± 6.3% | +21% | 5 | NS |
| 0.1% #2013 | 13.9 ± 7.3% | 36% | 5 | NS |
| 1.0% #2013 | 9.8 ± 2.0% | 55% | 5 | 0.004 |
| Experiment B | | | | |
| Vehicle | 23.5 ± 3.3% | — | 8 | — |
| 0.01% #2013 | 18.3 ± 4.0% | 22% | 8 | 0.01 |
| 0.1% #2013 | 14.6 ± 6.8% | 38% | 8 | 0.008 |
| 1.0% #2013 | 16.0 ± 3.6% | 32% | 8 | 0.0005 |

For comparison, topical application of 0.1 percent dexamethasone sodium phosphate resulted in 67 percent inhibition in neovascularization (p<<0.001) in Experiment B.

The formulation containing 1.0 percent of compound 2013 resulted in an average reduction in thymus weight of 27 percent (0.207±0.035 gm vs. 0.284±0.052 gm for controls; p=0.004). The formulation containing 0.1 percent compound 2013 had no significant effect on thymus weight. Body weight was unaffected by treatment with any concentration of this compound. In contrast, rats treated with topical 0.1 percent dexamethasone weighed 17 percent less than control rats at the end of the four days of treatment.

C. 17β-carboxylic acid derivative of hydrocortisone (compound 323). Only subjective angiogenesis scores were collected for this steroid. The mean ±1 standard deviation for the angiogenesis scores, average percent inhibition of neovascularization, number of rats per group, and p value (verses vehicle) are shown in Table 5.

TABLE 5

Corneal Angiogenesis for Compound 323

| Compound | Score | Percent Inhibition | n | p |
|---|---|---|---|---|
| Vehicle | 1.8 ± 0.6 | — | 8 | — |
| 0.01% #323 | 1.7 ± 1.1 | — | 7 | — |
| 0.1% #323 | 2.1 ± 0.5 | — | 7 | — |
| 1.0% #323 | 1.3 ± 0.9 | 28% | 7 | 0.08 |

During dissection, it was observed that angiogenesis was significantly suppressed by 1.0 present compound 323. If all eyes were included in the statistical analysis rather than the average of two eyes for each set, then the inhibition was significant (p=0.03).

D. 17β-carboxylic acid derivative of 6α-fluoro-dexamethasone (compound 532). The neovascularization study demonstrated the ability of this compound to inhibit corneal neovascularization. None of the groups given compound 532 varied significantly in body weight from the control group except the group receiving 0.1 percent 532; it is presumed that this result is erroneous, as no body weight change was observed. Also, thymus weight showed no significant difference between vehicle- and drug-treated groups.

The neovascularization results shown in Table 6 were obtained using the mean for both eyes of each rat (values are the mean ±1 standard deviation for corneal neovascularization expressed as the total length of blood vessels in the cornea).

TABLE 6

Corneal Angiogenesis Data for Compound 532

| Compound | Neovascularization | Percent Inhibition |
|---|---|---|
| Vehicle | 405.3 ± 33.2 | — |
| 0.01 percent #532 | 355.4 ± 62.2 | -12.3% |
| 0.1 percent #532 | 322.0 ± 78.0 | -20.6% |
| 1.0 percent #532 | 202.2 ± 74.3 | -50.1% |

Comparison using the Mann-Whitney U test (one-tailed) showed significant differences between vehicle and Compound 532 at all concentrations.

EXAMPLE 26

Angiogenesis Inhibition with Daily Administration

The ability of compounds 2013, 518, and 513 to inhibit corneal angiogenesis when injected subcutaneously once/day to was assessed on rats prepared as described in Example 8. Dexamethasone was used as a positive control. The results of this procedure are displayed in Table 7.

TABLE 7

Corneal Angiogenesis for Single Daily Dose of Steroid

| Compound/Dose (mg/kg/day) | Change in Body Wt (g) | Thymus Weight (g) | Neovasc. | n |
|---|---|---|---|---|
| Vehicle | −10.8 ± 10.0 | 0.412 ± 0.044 | 15.4 ± 3.2% | 4 |
| 2013 (10) | −5.2 ± 7.5 | 0.287 ± 0.087 | 21.5 ± 6.3% | 5 |
| 2013 (25) | −10.8 ± 7.5 | 0.264 ± 0.039 | 17.1 ± 3.0% | 4 |
| 518 (10) | −5.0 ± 10.0 | 0.321 ± 0.105 | 15.7 ± 5.8% | 5 |
| 513 (10) | −19.0 ± 7.7 | 0.125 ± 0.064 | 8.2 ± 1.1% | 4 |
| Dex. (1) | −27.4 ± 16.5 | 0.082 ± 0.029 | 9.3 ± 2.2% | 5 |

One-way analysis of variance was used to compare changes in body weight between drug-treated and vehicle groups; none of the drugs significantly altered body weight change. Thymus weight was significantly reduced by compound 2013 at 10 mg/kg/day (−30.3%; p=0.03, one-tailed) and 25 mg/kg/day (−35.9%; p=0.0025), compound 513 (−69.6%; p<0.001), and dexamethasone (−80.1%; p<0.001). Corneal neovascularization was only significantly reduced by compound 513 (−46.7%; p=0.015) and dexamethasone (−39.6%; (p=0.01).

EXAMPLE 27

Histological Study of Steroid-Treated Corneal Tissue

A histological study was performed in which either vehicle or 1 percent compound 2013 (17β-carboxylic acid derivative of prednisolone) was applied topically (QID) to rat corneas cauterized as described in Example 23. Five rats were included in each experimental group. The rats were killed either one or four days after treatment.

Histological sections were prepared through the cautery site. Neither corneal reepithelialization nor neovascularization were observed in any of the eyes from rats killed 24 hours after cautery. There was no difference in the degree of leukocytic infiltrate in the vehicle- and 2013-treated eyes at either 24 or 96 hours post-cautery. At 96 hours post-cautery, all corneas were reepithelialized; however, there was a marked reduction in neovascularization in the eyes treated with 2013 compared to the vehicle-treated eyes (0.6±0.6 vs. 2.6±0.7; p=0.004, one-tailed by rank sum test).

These data suggest that the effect compound 2013 exerts in reducing angiogenesis is not mediated by a reduction in leukocytic infiltrate.

EXAMPLE 28

Anti-tumor Activity

The HPAF tumor cell line is resistant to virtually all chemotherapeutic agents and grows rapidly in the nude mouse. Growth inhibition of this tumor for a period of time is thus indicative of significant anti-tumor activity.

Nude mice were implanted subcutaneously with 500,000 cells of the human pancreatic HPAF cell line. See Selvan et al., Drug Design and Discovery 9: 199–133 (1992). Treatment with 9α-fluoro-11β-hydroxy-16β-methyl-1,4-androstadien-3-one 17β-carboxylic acid steroid (20 mg/kg subcutaneously in 90 percent propylene glycol-ethanol, injected twice daily 6 days per week) was commenced the following day and continued for one month. Growth of tumor was inhibited for about 3 weeks compared to controls. After this point, rapid growth ensued.

The foregoing examples are illustrative of the present invention, and are not to be construed as limiting thereof. The invention is defined by the following claims, with equivalents of the claims to be included therein.

That which is claimed is:

1. A method of combatting a condition in a subject in need of such treatment, said condition being selected from the group consisting of angiogenesis, tumor growth, and ocular hypertension, said method comprising administering to said subject an effective condition-combatting amount of a compound of Formula I:

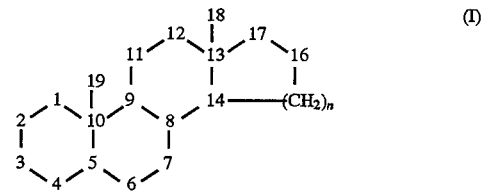

said compound being optionally substituted:

at position 1 from one to two times each with halogen, hydroxyl, lower alkyl, sulfo, phosphono, carboxyl, lower alkyloxyformyl, formamido, or lower alkanoyloxy;

at positions 2 and 4 from one or two times with: halogen; lower alkyl optionally substituted with phosphono, sulfo, hydroxy, lower alkanoyloxy, succinoyl, carbamoyl, or lower alkoxy; carboxyl; lower alkyloxyformyl; formamido; hydroxy; phosphono; sulfo; lower alkoxy; lower alkanoyloxy; succinoyl; carbamoyl; or methanoyl, or one time with oxo or lower alkylidene which is unsubstituted or substituted one time with methanoyl, carboxyl, lower alkyloxyformyl, or formamido;

at position 3 one or two times with:

lower alkyl optionally substituted with carboxyl, lower alkyloxyformyl, formamido, hydroxy, lower alkoxy, lower alkanoyloxy, succinoyl, carbamoyl, sulfo, phosphono, halogen, or methanoyl; hydroxyl; lower alkoxy; phosphono; sulfo; lower alkanoyloxy; succinoyl; carbamoyl; formamido; methanoyl; carboxyl; lower alkyloxyformyl; formamido; azide; or amine unsubstituted or substituted one time with lower alkyl, aryl or alkylaryl, or one time with: oxo; sulfur; oximo; lower alkyloximo; carboxymethyloximino; or lower alkylidene unsubstituted or substituted one time with alkoxy, hydroxy, lower alkanoyloxy, succinoyl, carbamoyl, sulfo, phosphono, carboxyl, lower alkyloxyformyl, or formamido;

at position 5 one time with methyl, lower alkoxy, or hydroxy;

at position 6 one or two times with: halogen; hydroxyl; lower alkoxy; lower alkanoyloxy; succinoyl; carbamoyl; sulfo; phosphono; cyano; methanoyl; oximino; lower alkyloximino; lower alkyl optionally substituted 1 to 3 times with halogen, hydroxyl, azide, or cyano; carboxyl; lower alkyloxyformyl; or formamido;

or one time with oxo, oximino, lower alkyloximino; or carboxymethyloximino;

at position 7 with lower alkyl, halogen, aryl, carboxyl, formamido, or lower alkyloxyformyl;

at position 9 one time with halogen, hydroxyl, halogenated lower alkyl, or lower alkyl;

at position 11 from one to two times with hydroxyl, lower alkoxy, lower alkanoyloxy, succinoyl, carbamoyl, halogenated lower alkanoyloxy, or lower alkyl, or one time with lower alkylidene or oxo;

at position 16 from one to two times with: lower alkyl optionally substituted one time with carboxyl, hydroxy, lower alkoxy, sulfo, or phosphono; halogenated lower alkyl; hydroxyl; lower alkoxy; lower alkanoyloxy; succinoyl; carbamoyl; sulfo; phosphono; nitroalkyl; cyano; carboxyl; lower alkyloxyformyl; formamido; or methanoyl; or one time with lower alkylidene optionally substituted one to three times with halogen or one time with oxo;

said compound being substituted at position 17 with a first substituent selected from the group consisting of:

lower alkyl which is optionally substituted with hydroxy, lower alkoxy, lower alkanoyloxy, succinoyl, carbamoyl, sulfo, phosphono, methanoyl, carboxyl, lower alkyloxyformyl, formamido, or amino optionally substituted 1 or 2 times with aryl or lower alkylcarbonyl; lower alkenyl optionally substituted one time with lower alkoxy; lower alkynyl; halogen; halogenated lower alkyl; hydroxy; alkoxy; alkanoyloxy; succinoyl; carbamoyl; sulfo; phosphono; methanoyl; carboxyl; lower alkyloxyformyl; formamido; carbonyl substituted with saturated or unsaturated lower alkyl optionally substituted with hydroxy, lower alkoxy, lower alkanoyloxy, succinoyl, carbamoyl, carboxyl, methanoyl, sulfo, phosphono, aryl, lower alkyloxyformyl, or formamido; hydroxymethyl substituted with aryl or with saturated or unsaturated lower alkyl optionally substituted with hydroxy, alkoxy, lower alkanoyloxy, succinoyl, carbamoyl, sulfo, phosphono, carboxyl, or methanoyl; aryl; aryloxy; aroyloxy; or amino optionally substituted 1 or 2 times with aryl or lower alkylcarbonyl;

and said compound being unsubstituted or substituted with a second substituent at position 17 selected from the group consisting of:

hydroxy; phosphono; sulfo; lower alkanoyloxy; saturated or unsaturated lower alkyl optionally substituted with hydroxy, lower alkoxy, lower alkanoyloxy, succinoyl, carbamoyl, phosphono, or sulfo; halogen; carboxyl; amino optionally substituted 1 or 2 times with aryl or lower alkylcarbonyl; azide; and cyano;

or wherein said compound is substituted so that positions 16 and 17 together form an unsubstituted or substituted isoxazolidine or methylene dioxy moiety;

or wherein position 17 is substituted one time with oxo, oximino, lower alkyloximino, carboxymethyloximino, or lower alkylidene substituted with hydroxy, lower alkanoyloxy, succinoyl, carbamoyl, sulfo, phosphono, carboxyl, lower alkyloxyformyl, or formamido;

at position 18 with lower alkyl;

at position 19 with lower alkyl optionally substituted with hydroxy, lower alkoxy, lower alkanoyloxy, succinoyl, carbamoyl, phosphono, sulfo, thio, lower alkylthio, lower alkylsulfo, carboxyl, lower alkyloxyformyl, formamido, or methanoyl;

n is 1 or 2;

wherein said compound can be unsaturated between positions 1 and 2, 2 and 3, 3 and 4, 4 and 5, 5 and 6, 6 and 7, 7 and 8, 8 and 9, 9 and 11, 11 and 12, 15 and 16, and 16 and 17;

wherein said compound can include epoxide moieties linked to each of positions 1 and 2, 2 and 3, 3 and 4, 4 and 5, 5 and 6, 6 and 7, 8 and 9, 9 and 11, 11 and 12, 15 and 16, and 16 and 17; and wherein exocyclic methylene groups optionally substituted 1 to 2 times with halogen may be linked to each of positions 1 and 2, 2 and 3, 3 and 4, 4 and 5, 5 and 6, 6 and 7, 7 and 8, 15 and 16, and 16 and 17;

or a pharmaceutical salt thereof.

2. A method according to claim 1, wherein said compound is substituted at position 6-α with halogen, halogenated lower alkyl, formyl, carboxyl, or cyano.

3. A method according to claim 1 further comprising the step of administering to said subject a glucocorticoid antagonist.

4. A method according to claim 1, wherein said compound is substituted at position 9-α with halogen or halogenated lower alkyl.

5. A method according to claim 1, wherein said compound is substituted at position 16 with lower alkyl.

6. A method according to claim 1, wherein said compound is unsaturated between positions 11 and 12.

7. A method according to claim 1, wherein said compound is unsaturated between positions 9 and 11.

8. A method according to claim 1, wherein said compound is substituted at position 2 with carboxyl.

9. A method according to claim 1, wherein n is 1.

10. A method according to claim 1, wherein said compound is substituted at position 17-β with carboxyl.

11. A method according to claim 1, wherein said compound is substituted at position 3 with hydroxyl, lower alkoxy, or lower alkanoyloxy.

12. A method of inhibiting angiogenesis in a subject in need of such treatment comprising administering to said subject an effective angiogenesis-combatting amount of a compound selected from the group consisting of:

(A) a compound of Formula IA:

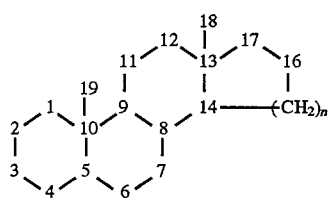

wherein said compound is substituted at position 6-α with halogen, and wherein said compound is optionally substituted:

- at position 1 from one to two times each with halogen, hydroxyl, lower alkyl, sulfo, phosphono, carboxyl, lower alkyloxyformyl, formamido, or lower alkanoyloxy;
- at positions 2 and 4 from one or two times with: halogen; lower alkyl optionally substituted with phosphono, sulfo, hydroxy, lower alkanoyloxy, succinoyl, carbamoyl, or lower alkoxy; carboxyl; lower alkyloxyformyl; formamido; hydroxy; phosphono; sulfo; lower alkoxy; lower alkanoyloxy; succinoyl; carbamoyl; or methanoyl, or
- one time with oxo or lower alkylidene which is unsubstituted or substituted one time with methanoyl, carboxyl, lower alkyloxyformyl, or formamido;
- at position 3 one or two times with:

lower alkyl optionally substituted with carboxyl, lower alkyloxyformyl, formamido, hydroxy, lower alkoxy, lower alkanoyloxy, succinoyl, carbamoyl, sulfo, phosphono, halogen, or methanoyl; hydroxyl; lower alkoxy; phosphono; sulfo; lower alkanoyloxy; succinoyl; carbamoyl; formamido; methanoyl; carboxyl; lower alkyloxyformyl; formamido; azide; or amine unsubstituted or substituted one time with lower alkyl, aryl or alkylaryl, or one time with: oxo; sulfur; oximo; lower alkyloximo; carboxymethyloximino; or lower alkylidene unsubstituted or substituted one time with alkoxy, hydroxy, lower alkanoyloxy, succinoyl, carbamoyl, sulfo, phosphono, carboxyl, lower alkyloxyformyl, or formamido;

- at position 5 one time with methyl, lower alkoxy, or hydroxy;
- at position 6β one time with: halogen; hydroxyl; lower alkoxy; lower alkanoyloxy; succinoyl; carbamoyl; sulfo; phosphono; cyano; methanoyl; oximino; lower alkyloximino; lower alkyl optionally substituted 1 to 3 times with halogen, hydroxyl, azide, or cyano; carboxyl; lower alkyloxyformyl; or formamido;
- at position 7 with lower alkyl, halogen, aryl, carboxyl, formamido, or lower alkyloxyformyl;
- at position 9 one time with halogen, hydroxyl, halogenated lower alkyl, or lower alkyl;
- at position 11 from one to two times with hydroxyl, lower alkoxy, lower alkanoyloxy, succinoyl, carbamoyl, halogenated lower alkanoyloxy, or lower alkyl, or one time with lower alkylidene or oxo;
- at position 16 from one to two times with: lower alkyl optionally substituted one time with carboxyl, hydroxy, lower alkoxy, sulfo, or phosphono; halogenated lower alkyl; hydroxyl; lower alkoxy; lower alkanoyloxy; succinoyl; carboxyl; sulfo; phosphono; nitroalkyl; cyano; carboxyl; lower alkyloxyformyl; formamido; or methanoyl; or one time with lower alkylidene optionally substituted one to three times with halogen or one time with oxo;

said compound being substituted at position 17 with a first substituent selected from the group consisting of:

lower alkyl which is optionally substituted with hydroxy, lower alkoxy, lower alkanoyloxy, succinoyl, carbamoyl, sulfo, phosphono, methanoyl, carboxyl, lower alkyloxyformyl, formamido, or amino optionally substituted 1 or 2 times with aryl or lower alkylcarbonyl; lower alkenyl optionally substituted one time with lower alkoxy; lower alkynyl; halogen; halogenated lower alkyl; hydroxy; alkoxy; alkanoyloxy; succinoyl; carbamoyl; sulfo; phosphono; methanoyl; carboxyl; lower alkyloxyformyl; formamido; carbonyl substituted with saturated or unsaturated lower alkyl optionally substituted with hydroxy, lower alkoxy, lower alkanoyloxy, succinoyl, carbamoyl, carboxyl, methanoyl, sulfo, phosphono, aryl, lower alkyloxyformyl, or formamido; hydroxymethyl substituted with aryl or with saturated or unsaturated lower alkyl optionally substituted with hydroxy, alkoxy, lower alkanoyloxy, succinoyl, carbamoyl, sulfo, phosphono, carboxyl, or methanoyl; aryl; aryloxy; aroyloxy; or amino optionally substituted 1 or 2 times with aryl or lower alkylcarbonyl;

and said compound being unsubstituted or substituted with a second substituent at position 17 selected from the group consisting of:

hydroxy; phosphono; sulfo; lower alkanoyloxy; saturated or unsaturated lower alkyl optionally substituted with hydroxy, lower alkoxy, lower alkanoyloxy, succinoyl, carbamoyl, phosphono, or sulfo; halogen; carboxyl; amino optionally substituted 1 or 2 times with aryl or lower alkylcarbonyl; azide; and cyano;

or wherein said compound is substituted so that positions 16 and 17 together form an unsubstituted or substituted isoxazolidine or methylene dioxy moiety;

or wherein position 17 is substituted one time with oxo, oximino, lower alkyloximino, carboxymethyloximino, or lower alkylidene substituted with hydroxy, lower alkanoyloxy, succinoyl, carbamoyl, sulfo, phosphono, carboxyl, lower alkyloxyformyl, or formamido;

at position 18 with lower alkyl;

at position 19 with lower alkyl optionally substituted with hydroxy, lower alkoxy, lower alkanoyloxy, succinoyl, carbamoyl, phosphono, sulfo, thio, lower alkylthio, lower alkylsulfo, carboxyl, lower alkyloxyformyl, formamido, or methanoyl;

n is 1 or 2;

wherein said compound can be unsaturated between positions 1 and 2, 2 and 3, 3 and 4, 4 and 5, 7 and 8, 8 and 9, 9 and 11, 11 and 12, 15 and 16, and 16 and 17;

wherein said compound can include epoxide moieties linked to each of positions 1 and 2, 2 and 3, 3 and 4, 4 and 5, 8 and 9, 9 and 11, 11 and 12, 15 and 16, and 16 and 17; and wherein exocyclic methylene groups optionally substituted 1 to 2 times with halogen may be linked to each of positions 1 and 2, 2 and 3, 3 and 4, 4 and 5, 7 and 8, 15 and 16, and 16 and 17;

or a pharmaceutical salt thereof;

(B) a compound of Formula IB:

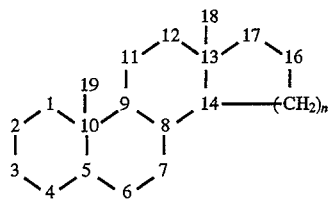

wherein said compound is substituted at position with halogen, and wherein said compound is further optionally substituted:

at position 1 from one to two times each with halogen, hydroxyl, lower alkyl, sulfo, phosphono, carboxyl, lower alkyloxyformyl, formamido, or lower alkanoyloxy;

at positions 2 and 4 from one or two times with: halogen; lower alkyl optionally substituted with phosphono, sulfo, hydroxy, lower alkanoyloxy, succinoyl, carbamoyl, or lower alkoxy; carboxyl; lower alkyloxyformyl; formamido; hydroxy; phosphono; sulfo; lower alkoxy; lower alkanoyloxy; succinoyl; carbamoyl; or methanoyl, or one time with oxo or lower alkylidene which is unsubstituted or substituted one time with methanoyl, carboxyl, lower alkyloxyformyl, or formamido;

at position 3 one or two times with:

lower alkyl optionally substituted with carboxyl, lower alkyloxyformyl, formamido, hydroxy, lower alkoxy, lower alkanoyloxy, succinoyl, carbamoyl, sulfo, phosphono, halogen, or methanoyl; hydroxyl; lower alkoxy; phosphono; sulfo; lower alkanoyloxy; succinoyl; carbamoyl; formamido; methanoyl; carboxyl; lower alkyloxyformyl; formamido; azide; or amine unsubstituted or substituted one time with lower alkyl, aryl or alkylaryl, or one time with: oxo; sulfur; oximo; lower alkyloximo; carboxymethyloximino; or lower alkylidene unsubstituted or substituted one time with alkoxy, hydroxy, lower alkanoyloxy, succinoyl, carbamoyl, sulfo, phosphono, carboxyl, lower alkyloxyformyl, or formamido;

at position 5 one time with methyl, lower alkoxy, or hydroxy;

at position 6 one or two times with: halogen; hydroxyl; lower alkoxy; lower alkanoyloxy; succinoyl; carbamoyl; sulfo; phosphono; cyano; methanoyl; oximino; lower alkyloximino; lower alkyl optionally substituted 1 to 3 times with halogen, hydroxyl, azide, or cyano; carboxyl; lower alkyloxyformyl; or formamido;

or one time with oxo, oximino, lower alkyloximino; or carboxymethyloximino;

at position 7 with lower alkyl, halogen, aryl, carboxyl, formamido, or lower alkyloxyformyl;

at position 11 from one to two times with hydroxyl, lower alkoxy, lower alkanoyloxy, succinoyl, carbamoyl, halogenated lower alkanoyloxy, or lower alkyl, or one time with lower alkylidene or oxo;

at position 16 from one to two times with: lower alkyl optionally substituted one time with carboxyl, hydroxy, lower alkoxy, sulfo, or phosphono; halogenated lower alkyl; hydroxyl; lower alkoxy; lower alkanoyloxy; succinoyl; carbamoyl; sulfo; phosphono; nitroalkyl; cyano; carboxyl; lower alkyloxyformyl; formamido; or methanoyl; or one time with lower alkylidene optionally substituted one to three times with halogen or one time with oxo;

said compound being substituted at position 17 with a first substituent selected from the group consisting of:

lower alkyl which is optionally substituted with hydroxy, lower alkoxy, lower alkanoyloxy, succinoyl, carbamoyl, sulfo, phosphono, methanoyl, carboxyl, lower alkyloxyformyl, formamido, or amino optionally substituted 1 or 2 times with aryl or lower alkylcarbonyl; lower alkenyl optionally substituted one time with lower alkoxy; lower alkynyl; halogen; halogenated lower alkyl; hydroxy; alkoxy; alkanoyloxy; succinoyl; carbamoyl; sulfo; phosphono; methanoyl; carboxyl; lower alkyloxyformyl; formamido; carbonyl substituted with saturated or unsaturated lower alkyl optionally substituted with hydroxy, lower alkoxy, lower alkanoyloxy, succinoyl, carbamoyl, carboxyl, methanoyl, sulfo, phosphono, aryl, lower alkyloxyformyl, or formamido; hydroxymethyl substituted with aryl or with saturated or unsaturated lower alkyl optionally substituted with hydroxy, alkoxy, lower alkanoyloxy, succinoyl, carbamoyl, sulfo, phosphono, carboxyl, or methanoyl; aryl; aryloxy; aroyloxy; or amino optionally substituted 1 or 2 times with aryl or lower alkylcarbonyl;

and said compound being unsubstituted or substituted with a second substituent at position 17 selected from the group consisting of:

hydroxy; phosphono; sulfo; lower alkanoyloxy; succinoyl; carbamoyl; saturated or unsaturated lower alkyl optionally substituted with hydroxy, lower alkoxy, lower alkanoyloxy, succinoyl, carbamoyl, phosphono, or sulfo; halogen; carboxyl; amino optionally substituted 1 or 2 times with aryl or lower alkylcarbonyl; azide; and cyano;

or wherein said compound is substituted so that positions 16 and 17 together form an unsubstituted or substituted isoxazolidine or methylene dioxy moiety;

or wherein position 17 is substituted one time with oxo, oximino, lower alkyloximino, carboxymethyloximino, or lower alkylidene substituted with hydroxy, lower alkanoyloxy, succinoyl, carbamoyl, sulfo, phosphono, carboxyl, lower alkyloxyformyl, or formamido;

at position 18 with lower alkyl;

at position 19 with lower alkyl optionally substituted with hydroxy, lower alkoxy, lower alkanoyloxy, succinoyl, carbamoyl, phosphono, sulfo, thio, lower alkylthio, lower alkylsulfo, carboxyl, lower alkyloxyformyl, formamido, or methanoyl;

n is 1 or 2;

wherein said compound can be unsaturated between positions 1 and 2, 2 and 3, 3 and 4, 4 and 5, 5 and 6, 6 and 7, 7 and 8, 11 and 12, 15 and 16, and 16 and 17;

wherein said compound can include epoxide moieties linked to each of positions 1 and 2, 2 and 3, 3 and 4, 4 and 5, 5 and 6, 6 and 7, 11 and 12, 15 and 16, and 16 and 17; and wherein exocyclic methylene groups optionally substituted 1 to 2 times with halogen may be linked to each of positions 1 and 2, 2 and 3, 3 and 4, 4 and 5, 5 and 6, 6 and 7, 7 and 8, 15 and 16, and 16 and 17;

or a pharmaceutical salt thereof;

(C) a compound of Formula IC:

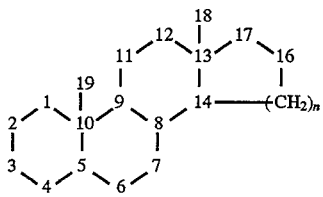

wherein said compound is substituted at position 16 with methyl or methylene, and wherein said compound is optionally substituted:

at position 1 from one to two times each with halogen, hydroxyl, lower alkyl, sulfo, phosphono, carboxyl, lower alkyloxyformyl, formamido, or lower alkanoyloxy;

at positions 2 and 4 from one or two times with: halogen; lower alkyl optionally substituted with phosphono, sulfo, hydroxy, lower alkanoyloxy, succinoyl, carbamoyl, or lower alkoxy; carboxyl; lower alkyloxyformyl; formamido; hydroxy; phosphono; sulfo; lower alkoxy; lower alkanoyloxy; succinoyl; carbamoyl; or methanoyl, or one time with oxo or lower alkylidene which is unsubstituted or substituted one time with methanoyl, carboxyl, lower alkyloxyformyl, or formamido;

at position 3 one or two times with:

lower alkyl optionally substituted with carboxyl, lower alkyloxyformyl, formamido, hydroxy, lower alkoxy, lower alkanoyloxy, succinoyl, carbamoyl, sulfo, phosphono, halogen, or methanoyl; hydroxyl; lower alkoxy; phosphono; sulfo; lower alkanoyloxy; succinoyl; carbamoyl; formamido; methanoyl; carboxyl; lower alkyloxyformyl; formamido; azide; or amine unsubstituted or substituted one time with lower alkyl, aryl or alkylaryl, or one time with: oxo; sulfur; oximo; lower alkyloximo; carboxymethyloximino; or lower alkylidene unsubstituted or substituted one time with alkoxy, hydroxy, lower alkanoyloxy, succinoyl, carbamoyl, sulfo, phosphono, carboxyl, lower alkyloxyformyl, or formamido;

at position 5 one time with methyl, lower alkoxy, or hydroxy;

at position 6 one or two times with: halogen; hydroxyl; lower alkoxy; lower alkanoyloxy; succinoyl; carbamoyl; sulfo; phosphono; cyano; methanoyl; oximino; lower alkyloximino; lower alkyl optionally substituted 1 to 3 times with halogen, hydroxyl, azide, or cyano; carboxyl; lower alkyloxyformyl; or formamido;

or one time with oxo, oximino, lower alkyloximino; or carboxymethyloximino;

at position 7 with lower alkyl, halogen, aryl, carboxyl, formamido, or lower alkyloxyformyl;

at position 9 one time with halogen, hydroxyl, halogenated lower alkyl, or lower alkyl;

at position 11 from one to two times with hydroxyl, lower alkoxy, lower alkanoyloxy, succinoyl, carbamoyl, halogenated lower alkanoyloxy, or lower alkyl, or one time with lower alkylidene or oxo;

said compound being substituted at position 17 with a first substituent selected from the group consisting of:

lower alkyl which is optionally substituted with hydroxy, lower alkoxy, lower alkanoyloxy, succinoyl, carbamoyl, sulfo, phosphono, methanoyl, carboxyl, lower alkyloxyformyl, formamido, or amino optionally substituted 1 or 2 times with aryl or lower alkylcarbonyl; lower alkenyl optionally substituted one time with lower alkoxy; lower alkynyl; halogen; halogenated lower alkyl; hydroxy; alkoxy; alkanoyloxy; succinoyl; carbamoyl; sulfo; phosphono; methanoyl; carboxyl; lower alkyloxyformyl; formamido; carbonyl substituted with saturated or unsaturated lower alkyl optionally substituted with hydroxy, lower alkoxy, lower alkanoyloxy, succinoyl, carbamoyl, carboxyl, methanoyl, sulfo, phosphono, aryl, lower alkyloxyformyl, or formamido; hydroxymethyl substituted with aryl or with saturated or unsaturated lower alkyl optionally substituted with hydroxy, alkoxy, lower alkanoyloxy, succinoyl, carbamoyl, sulfo, phosphono, carboxyl, or methanoyl; aryl; aryloxy; aroyloxy; or amino optionally substituted 1 or 2 times with aryl or lower alkylcarbonyl;

and said compound being unsubstituted or substituted with a second substituent at position 17 selected from the group consisting of:

hydroxy; phosphono; sulfo; lower alkanoyloxy; succinoyl; carbamoyl; saturated or unsaturated lower alkyl optionally substituted with hydroxy, lower alkoxy, lower alkanoyloxy, succinoyl, carbamoyl, phosphono, or sulfo; halogen; carboxyl; amino optionally substituted 1 or 2 times with aryl or lower alkylcarbonyl; azide; and cyano;

or wherein position 17 is substituted one time with oxo, oximino, lower alkyloximino, carboxymethyloximino, or lower alkylidene substituted with hydroxy, lower alkanoyloxy, succinoyl, carbamoyl, sulfo, phosphono, carboxyl, lower alkyloxyformyl, or formamido;

at position 18 with lower alkyl;

at position 19 with lower alkyl optionally substituted with hydroxy, lower alkoxy, lower alkanoyloxy, succinoyl, carbamoyl, phosphono, sulfo, thio, lower alkylthio, lower alkylsulfo, carboxyl, lower alkyloxyformyl, formamido, or methanoyl;

n is 1 or 2;

wherein said compound can be unsaturated between positions 1 and 2, 2 and 3, 3 and 4, 4 and 5, 5 and 6, 6 and 7, 7 and 8, 8 and 9, 9 and 11, and 11 and 12;

wherein said compound can include epoxide moieties linked to each of positions 1 and 2, 2 and 3, and 4, 4 and 5, 5 and 6, 6 and 7, 8 and 9, 9 and 11, 3 and 11 and 12; and wherein exocyclic methylene groups optionally substituted 1 to 2 times with halogen may be linked to each of positions 1 and 2, 2 and 3, 3 and 4, 4 and 5, 5 and 6, 6 and 7, and 7 and 8;

or a pharmaceutical salt thereof;

(D) a compound of Formula ID:

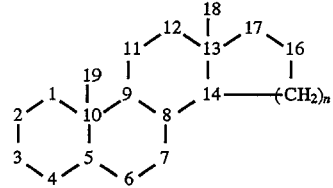

wherein said compound is unsaturated between positions 9 and 11, and wherein said compound is optionally substituted:

at position 1 from one to two times each with halogen, hydroxyl, lower alkyl, sulfo, phosphono, carboxyl, lower alkyloxyformyl, formamido, or lower alkanoyloxy;

at positions 2 and 4 from one or two times with: halogen; lower alkyl optionally substituted with phosphono, sulfo, hydroxy, lower alkanoyloxy, succinoyl, carbamoyl, or lower alkoxy; carboxyl; lower alkyloxyformyl; formamido; hydroxy; phosphono; sulfo; lower alkoxy; lower alkanoyloxy; succinoyl; carbamoyl; or methanoyl, or one time with oxo or lower alkylidene which is unsubstituted or substituted one time with methanoyl, carboxyl, lower alkyloxyformyl, or formamido;

at position 3 one or two times with:

lower alkyl optionally substituted with carboxyl, lower alkyloxyformyl, formamido, hydroxy, lower alkoxy, lower alkanoyloxy, succinoyl, carbamoyl, sulfo, phosphono, halogen, or methanoyl; hydroxyl; lower alkoxy; phosphono; sulfo; lower alkanoyloxy; succinoyl; carbamoyl; formamido; methanoyl; carboxyl; lower alkyloxyformyl; formamido; azide; or amine unsubstituted or substituted one time with lower alkyl, aryl or alkylaryl, or one time with: oxo; sulfur; oximo; lower alkyloximo; carboxymethyloximino; or lower alkylidene unsubstituted or substituted one time with alkoxy, hydroxy, lower alkanoyloxy, succinoyl, carbamoyl, sulfo, phosphono, carboxyl, lower alkyloxyformyl, or formamido;

at position 5 one time with methyl, lower alkoxy, or hydroxy;

at position 6 one or two times with: halogen; hydroxyl; lower alkoxy; lower alkanoyloxy; succinoyl; carbamoyl; sulfo; phosphono; cyano; methanoyl; oximino; lower alkyloximino; lower alkyl optionally substituted 1 to 3 times with halogen, hydroxyl, azide, or cyano; carboxyl; lower alkyloxyformyl; or formamido;

or one time with oxo, oximino, lower alkyloximino; or carboxymethyloximino;

at position 7 with lower alkyl, halogen, aryl, carboxyl, formamido, or lower alkyloxyformyl;

at position 11 one time with hydroxyl, lower alkoxy, lower alkanoyloxy, succinoyl, carbamoyl, halogenated lower alkanoyloxy, or lower alkyl;

at position 16 from one to two times with: lower alkyl optionally substituted one time with carboxyl, hydroxy, lower alkoxy, sulfo, or phosphono; halogenated lower alkyl; hydroxyl; lower alkoxy; lower alkanoyloxy; succinoyl; carbamoyl; sulfo; phosphono; nitroalkyl; cyano; carboxyl; lower alkyloxyformyl; formamido; or methanoyl; or one time with lower alkylidene optionally substituted one to three times with halogen or one time with oxo;

said compound being substituted at position 17 with a first substituent selected from the group consisting of:

lower alkyl which is optionally substituted with hydroxy, lower alkoxy, lower alkanoyloxy, succinoyl, carbamoyl, sulfo, phosphono, methanoyl, carboxyl, lower alkyloxyformyl, formamido, or amino optionally substituted 1 or 2 times with aryl or lower alkylcarbonyl; lower alkenyl optionally substituted one time with lower alkoxy; lower alkynyl; halogen; halogenated lower alkyl; hydroxy; alkoxy; alkanoyloxy; succinoyl; carbamoyl; sulfo; phosphono; methanoyl; carboxyl; lower alkyloxyformyl; formamido; carbonyl substituted with saturated or unsaturated lower alkyl optionally substituted with hydroxy, lower alkoxy, lower alkanoyloxy, succinoyl, carbamoyl, carboxyl, methanoyl, sulfo, phosphono, aryl, lower alkyloxyformyl, or formamido; hydroxymethyl substituted with aryl or with saturated or unsaturated lower alkyl optionally substituted with hydroxy, alkoxy, lower alkanoyloxy, succinoyl, carbamoyl, sulfo, phosphono, carboxyl, or methanoyl; aryl; aryloxy; aroyloxy; or amino optionally substituted 1 or 2 times with aryl or lower alkylcarbonyl;

and said compound being unsubstituted or substituted with a second substituent at position 17 selected from the group consisting of:

hydroxy; phosphono; sulfo; lower alkanoyloxy; succinoyl; carbamoyl; saturated or unsaturated lower alkyl optionally substituted with hydroxy, lower alkoxy, lower alkanoyloxy, succinoyl, carbamoyl, phosphono, or sulfo; halogen; carboxyl; amino optionally substituted 1 or 2 times with aryl or lower alkylcarbonyl; azide; and cyano;

or wherein said compound is substituted so that positions 16 and 17 together form an unsubstituted or substituted isoxazolidine or methylene dioxy moiety;

or wherein position 17 is substituted one time with oxo, oximino, lower alkyloximino, carboxymethyloximino, or lower alkylidene substituted with hydroxy, lower alkanoyloxy, succinoyl, carbamoyl, sulfo, phosphono, carboxyl, lower alkyloxyformyl, or formamido;

at position 18 with lower alkyl;

at position 19 with lower alkyl optionally substituted with hydroxy, lower alkoxy, lower alkanoyloxy, succinoyl, carbamoyl, phosphono, sulfo, thio, lower alkylthio, lower alkylsulfo, carboxyl, lower alkyloxyformyl, formamido, or methanoyl;

n is 1 or 2;

wherein said compound can be unsaturated between positions 1 and 2, 2 and 3, 3 and 4, 4 and 5, 5 and 6, 6 and 7, 7 and 8, 15 and 16, and 16 and 17;

wherein said compound can include epoxide moieties linked to each of positions 1 and 2, 2 and 3, 3 and 4, 4 and 5, 5 and 6, 6 and 7, 15 and 16, and 16 and 17; and wherein exocyclic methylene groups optionally substituted 1 to 2 times with halogen may be linked to each of positions 1 and 2, 2 and 3, 3 and 4, 4 and 5, 5 and 6, 6 and 7, 7 and 8, 15 and 16, and 16 and 17;

or a pharmaceutical salt thereof;

(E) a compound of Formula IE:

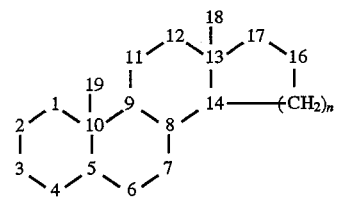

wherein said compound is substituted at position 2 with carboxyl, lower alkyloxyformyl, or formamido, and wherein said compound is optionally substituted:

at position 1 from one to two times each with halogen, hydroxyl, lower alkyl, sulfo, phosphono, carboxyl, lower alkyloxyformyl, formamido, or lower alkanoyloxy;

at position 4 from one or two times with: halogen; lower alkyl optionally substituted with phosphono, sulfo, hydroxy, lower alkanoyloxy, succinoyl, carbamoyl, or lower alkoxy; carboxyl; lower alkyloxyformyl; formamido; hydroxy; phosphono; sulfo; lower alkoxy; lower alkanoyloxy; succinoyl; carbamoyl; or methanoyl, or one time with oxo or lower alkylidene which is unsubstituted or substituted one time with methanoyl, carboxyl, lower alkyloxyformyl, or formamido;

at position 3 one or two times with:

lower alkyl optionally substituted with carboxyl, lower alkyloxyformyl, formamido, hydroxy, lower alkoxy, lower alkanoyloxy, succinoyl, carbamoyl, sulfo, phosphono, halogen, or methanoyl; hydroxyl; lower alkoxy; phosphono; sulfo; lower alkanoyloxy; succinoyl; carbamoyl; formamido; methanoyl; carboxyl; lower alkyloxyformyl; formamido; azide; or amine unsubstituted or substituted one time with lower alkyl, aryl or alkylaryl, or one time with: oxo; sulfur; oximo; lower alkyloximo; carboxymethyloximino; or lower alkylidene unsubstituted or substituted one time with alkoxy, hydroxy, lower alkanoyloxy, succinoyl, carbamoyl, sulfo, phosphono, carboxyl, lower alkyloxyformyl, or formamido;

at position 5 one time with methyl, lower alkoxy, or hydroxy;

at position 6 one or two times with: halogen; hydroxyl; lower alkoxy; lower alkanoyloxy; succinoyl; carbamoyl; sulfo; phosphono; cyano; methanoyl; oximino; lower alkyloximino; lower alkyl optionally substituted 1 to 3 times with halogen, hydroxyl, azide, or cyano; carboxyl; lower alkyloxyformyl; or formamido;

or one time with oxo, oximino, lower alkyloximino; or carboxymethyloximino;

at position 7 with lower alkyl, halogen, aryl, carboxyl, formamido, or lower alkyloxyformyl;

at position 9 one time with halogen, hydroxyl, halogenated lower alkyl, or lower alkyl;

at position 11 from one to two times with hydroxyl, lower alkoxy, lower alkanoyloxy, succinoyl, carbamoyl, halogenated lower alkanoyloxy, or lower alkyl, or one time with lower alkylidene or oxo;

at position 16 from one to two times with: lower alkyl optionally substituted one time with carboxyl, hydroxy, lower alkoxy, sulfo, or phosphono; halogenated lower alkyl; hydroxyl; lower alkoxy; lower 555 alkanoyloxy; succinoyl; carbamoyl; sulfo; phosphono; nitroalkyl; cyano; carboxyl; lower alkyloxyformyl; formamido; or methanoyl; or one time with lower alkylidene optionally substituted one to three times with halogen or one time with oxo;

said compound being substituted at position 17 with a first substituent selected from the group consisting of:

lower alkyl which is optionally substituted with hydroxy, lower alkoxy, lower alkanoyloxy, succinoyl, carbamoyl, sulfo, phosphono, methanoyl, carboxyl, lower alkyloxyformyl, formamido, or amino optionally substituted 1 or 2 times with aryl or lower alkylcarbonyl; lower alkenyl optionally substituted one time with lower alkoxy; lower alkynyl; halogen; halogenated lower alkyl; hydroxy; alkoxy; alkanoyloxy; succinoyl; carbamoyl; sulfo; phosphono; methanoyl; carboxyl; lower alkyloxyformyl; formamido; carbonyl substituted with saturated or unsaturated lower alkyl optionally substituted with hydroxy, lower alkoxy, lower alkanoyloxy, succinoyl, carbamoyl, carboxyl, methanoyl, sulfo, phosphono, aryl, lower alkyloxyformyl, or formamido; hydroxymethyl substituted with aryl or with saturated or unsaturated lower alkyl optionally substituted with hydroxy, alkoxy, lower alkanoyloxy, succinoyl, carbamoyl, sulfo, phosphono, carboxyl, or methanoyl; aryl; aryloxy; aroyloxy; or amino optionally substituted 1 or 2 times with aryl or lower alkylcarbonyl;

and said compound being unsubstituted or substituted with a second substituent at position 17 selected from the group consisting of:

hydroxy; phosphono; sulfo; lower alkanoyloxy; succinoyl; carbamoyl; saturated or unsaturated lower alkyl optionally substituted with hydroxy, lower alkoxy, lower alkanoyloxy, succinoyl, carbamoyl, phosphono, or sulfo; halogen; carboxyl; amino optionally substituted 1 or 2 times with aryl or lower alkylcarbonyl; azide; and cyano;

or wherein said compound is substituted so that positions 16 and 17 together form an unsubstituted or substituted isoxazolidine or methylene dioxy moiety;

or wherein position 17 is substituted one time with oxo, oximino, lower alkyloximino, carboxymethyloximino, or lower alkylidene substituted with hydroxy, lower alkanoyloxy, succinoyl, carbamoyl, sulfo, phosphono, carboxyl, lower alkyloxyformyl, or formamido;

at position 18 with lower alkyl;

at position 19 with lower alkyl optionally substituted with hydroxy, lower alkoxy, lower alkanoyloxy, succinoyl, carbamoyl, phosphono, sulfo, thio, lower alkylthio, lower alkylsulfo, carboxyl, lower alkyloxyformyl, formamido, or methanoyl;

n is 1 or 2;

wherein said compound can be unsaturated between positions 1 and 2, 2 and 3, 3 and 4, 4 and 5, 5 and 6, 6 and 7, 7 and 8, 8 and 9, 9 and 11, 11 and 12, 15 and 16, and 16 and 17;

wherein said compound can include epoxide moieties linked to each of positions 1 and 2, 2 and 3, 3 and 4, 4 and 5, 5 and 6, 6 and 7, 8 and 9, 9 and 11, 11 and 12, 15 and 16, and 16 and 17; and wherein exocyclic methylene groups optionally substituted 1 to 2 times with halogen may be linked to each of positions 1 and 2, 2 and 3, 3 and 4, 4 and 5, 5 and 6, 6 and 7, 7 and 8, 15 and 16, and 16 and 17;

or a pharmaceutical salt thereof; and (F) a compound of Formula IF:

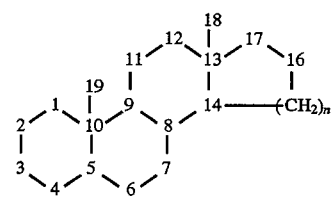

said compound being optionally substituted:

at position 1 from one to two times each with halogen, hydroxyl, lower alkyl, sulfo, phosphono, carboxyl, lower alkyloxyformyl, formamido, or lower alkanoyloxy;

at positions 2 and 4 from one or two times with: halogen; lower alkyl optionally substituted with phosphono, sulfo, hydroxy, lower alkanoyloxy, succinoyl, carbamoyl, or lower alkoxy; carboxyl; lower alkyloxyformyl; formamido; hydroxy; phosphono; sulfo; lower alkoxy; lower alkanoyloxy; succinoyl; carbamoyl; or methanoyl, or one time with oxo or lower alkylidene which is unsubstituted or substituted one time with methanoyl, carboxyl, lower alkyloxyformyl, or formamido;

at position 3 one or two times with:

lower alkyl optionally substituted with carboxyl, lower alkyloxyformyl, formamido, hydroxy, lower alkoxy, lower alkanoyloxy, succinoyl, carbamoyl, sulfo, phosphono, halogen, or methanoyl; hydroxyl; lower alkoxy; phosphono; sulfo; lower alkanoyloxy; succinoyl; carbamoyl; formamido; methanoyl; carboxyl; lower alkyloxyformyl; formamido; azide; or amine unsubstituted or substituted one time with lower alkyl, aryl or alkylaryl, or one time with: oxo; sulfur; oximo; lower alkyloximo; carboxymethyloximino; or lower alkylidene unsubstituted or substituted one time with alkoxy, hydroxy, lower alkanoyloxy, succinoyl, carbamoyl, sulfo, phosphono, carboxyl, lower alkyloxyformyl, or formamido;

at position 5 one time with methyl, lower alkoxy, or hydroxy;

at position 6 one or two times with: halogen; hydroxyl; lower alkoxy; lower alkanoyloxy; succinoyl; carbamoyl; sulfo; phosphono; cyano; methanoyl; oximino; lower alkyloximino; lower alkyl optionally substituted 1 to 3 times with halogen, hydroxyl, azide, or cyano; carboxyl; lower alkyloxyformyl; or formamido;

or one time with oxo, oximino, lower alkyloximino; or carboxymethyloximino;

at position 7 with lower alkyl, halogen, aryl, carboxyl, formamido, or lower alkyloxyformyl;

at position 9 one time with halogen, hydroxyl, halogenated lower alkyl, or lower alkyl;

at position 11 from one to two times with hydroxyl, lower alkoxy, lower alkanoyloxy, succinoyl, carbamoyl, halogenated lower alkanoyloxy, or lower alkyl, or one time with lower alkylidene or oxo;

at position 16 from one to two times with: lower alkyl optionally substituted one time with carboxyl, hydroxy, lower alkoxy, sulfo, or phosphono; halogenated lower alkyl; hydroxyl; lower alkoxy; lower alkanoyloxy; succinoyl; carbamoyl; sulfo; phosphono; nitroalkyl; cyano; carboxyl; lower alkyloxyformyl; formamido; or methanoyl; or one time with lower alkylidene optionally substituted one to three times with halogen or one time with oxo;

said compound being substituted at position 17 with a first substituent selected from the group consisting of:

carboxyl; alkyloxyformyl; alkylformamido; methanoyl; or carbonyl substituted with saturated or unsaturated lower alkyl which is optionally substituted with hydroxy, lower alkoxy, lower alkanoyloxy, succinoyl, carbamoyl, sulfo, or phosphono;

and said compound being unsubstituted or substituted with a second substituent at position 17 selected from the group consisting of:

hydroxy; phosphono; sulfo; lower alkanoyloxy; succinoyl; carbamoyl; saturated or unsaturated lower alkyl optionally substituted with hydroxy, lower alkoxy, lower alkanoyloxy, succinoyl, carbamoyl, phosphono, or sulfo; halogen; carboxyl; amino optionally substituted 1 or 2 times with aryl or lower alkylcarbonyl; azide; and cyano;

at position 18 with lower alkyl;

at position 19 with lower alkyl optionally substituted with hydroxy, lower alkoxy, lower alkanoyloxy, succinoyl, carbamoyl, phosphono, sulfo, thio, lower alkylthio, lower alkylsulfo, carboxyl, lower alkyloxyformyl, formamido, or methanoyl;

n is 1 or 2;

wherein said compound can be unsaturated between positions 1 and 2, 2 and 3, 3 and 4, 4 and 5, 5 and 6, 6 and 7, 8 and 9, 9 and 11, 11 and 12, 15 and 16, and 16 and 17;

wherein said compound can include epoxide moieties linked to each of positions 1 and 2, 2 and 3, 3 and 4, 4 and 5, 5 and 6, 6 and 7, 8 and 9, 9 and 11, 11 and 12, 15 and 16, and 16 and 17; and wherein exocyclic methylene groups optionally substituted 1 to 2 times with halogen may be linked to each of positions 1 and 2, 2 and 3, 3 and 4, 4 and 5, 5 and 6, 6 and 7, 7 and 8, 15 and 16, and 16 and 17;

or a pharmaceutical salt thereof.

13. A method according to claim 12, wherein said compound is 6,9-difluoro-11β,17-dihydroxy-16α-methyl-pregna-1,4-diene-3-one-17-carboxylic acid.

* * * * *

UNITED STATES PATENT AND TRADEMARK OFFICE
CERTIFICATE OF CORRECTION

PATENT NO. : 5,646,136
DATED : July 8, 1997
INVENTOR(S) : Petrow et al.

It is certified that error appears in the above-indentified patent and that said Letters Patent is hereby corrected as shown below:

Column 1, line 5,

--This invention was made with government support under R01 EY05883 awarded by the National Institutes of Health. The government has certain rights in the invention.--

Signed and Sealed this

Fourteenth Day of October, 1997

Attest:

BRUCE LEHMAN

*Attesting Officer*  *Commissioner of Patents and Trademarks*